(12) United States Patent
Coyle et al.

(10) Patent No.: US 7,267,652 B2
(45) Date of Patent: Sep. 11, 2007

(54) SYSTEMS AND METHODS FOR RESPIRATORY EVENT DETECTION

(75) Inventors: Michael Coyle, Ventura, CA (US); Desmond B. Keenan, Santa Barbara, CA (US); P. Alexander Derchak, Summit, NJ (US); Marvin Sackner, Miami Beach, FL (US); Frank Wilhelm, Riehen (CH); Keith Gilroy, Upland, CA (US); Emerance M. Gummels, Miramar, FL (US); Dana Michael Inman, Seabrook, TX (US); Paul Kennedy, Ojai, CA (US); Mark Mitchnick, East Hampton, NY (US); Andrew Behar, Ojai, CA (US)

(73) Assignee: VivoMetrics, Inc., Ventura, CA (US)

( * ) Notice: Subject to any disclaimer, the term of this patent is extended or adjusted under 35 U.S.C. 154(b) by 291 days.

(21) Appl. No.: 10/822,260

(22) Filed: Apr. 9, 2004

(65) Prior Publication Data

US 2005/0119586 A1 Jun. 2, 2005

Related U.S. Application Data

(60) Provisional application No. 60/506,904, filed on Sep. 26, 2003, provisional application No. 60/461,738, filed on Apr. 10, 2003.

(51) Int. Cl.
*A61B 5/08* (2006.01)

(52) U.S. Cl. ........................................ 600/538; 600/529

(58) Field of Classification Search ........... 128/200.24, 128/204.23; 600/300, 301, 409, 508, 529, 600/532, 534, 535, 536, 538, 561, 586, 587, 600/595

See application file for complete search history.

(56) References Cited

U.S. PATENT DOCUMENTS

| | | | |
|---|---|---|---|
| 4,308,872 A | 1/1982 | Watson et al. | |
| 4,373,534 A | 2/1983 | Watson | |
| 4,452,252 A | 6/1984 | Sackner | |
| 4,456,015 A | 6/1984 | Sackner | |
| 4,463,764 A * | 8/1984 | Anderson et al. | 600/532 |
| 4,648,407 A | 3/1987 | Sackner | |

(Continued)

*Primary Examiner*—Charles A. Marmor, II
*Assistant Examiner*—Karen E Toth
(74) *Attorney, Agent, or Firm*—Winston & Strawn LLP

(57) ABSTRACT

The present invention is directed to improved systems and methods for processing respiratory signals derived generally from respiratory plethysmography, and especially from respiratory inductive plethysmographic sensors mounted on a garment for ambulatory recording. The systems and methods provide improved signal filtering for artifact rejection, improved calibration of sensor data to produce outputs indicative of lung volumes. Further, this invention provides improved systems and methods directed to processing lung volume signals, however measured or derived, to provide improved determination of respiratory parameters and improved recognition of selected respiratory events.

24 Claims, 17 Drawing Sheets

U.S. PATENT DOCUMENTS

| | | |
|---|---|---|
| 4,777,962 A | 10/1988 | Watson et al. |
| 4,796,639 A * | 1/1989 | Snow et al. ................. 600/532 |
| 4,807,640 A | 2/1989 | Watson et al. |
| 4,815,473 A | 3/1989 | Watson et al. |
| 4,834,109 A * | 5/1989 | Watson ....................... 600/534 |
| 4,860,766 A | 8/1989 | Sackner |
| 4,986,277 A | 1/1991 | Sackner |
| 5,040,540 A | 8/1991 | Sackner |
| 5,159,935 A | 11/1992 | Sackner et al. |
| 5,178,151 A | 1/1993 | Sackner |
| 5,301,678 A | 4/1994 | Watson et al. |
| 5,331,968 A | 7/1994 | Williams et al. |
| 5,348,008 A | 9/1994 | Bornn et al. |
| 5,353,793 A | 10/1994 | Bornn et al. |
| 5,588,425 A | 12/1996 | Sackner et al. |
| 6,015,388 A * | 1/2000 | Sackner et al. .............. 600/529 |
| 6,047,203 A | 4/2000 | Sackner et al. |
| 6,261,238 B1 * | 7/2001 | Gavriely ...................... 600/532 |
| 6,341,504 B1 | 1/2002 | Istook |
| 6,413,225 B1 | 7/2002 | Sackner et al. |
| 6,436,057 B1 * | 8/2002 | Goldsmith et al. .......... 600/586 |
| 6,551,252 B2 | 4/2003 | Sackner et al. |
| 6,783,498 B2 | 8/2004 | Sackner et al. |
| 2004/0111040 A1 * | 6/2004 | Ni et al. ...................... 600/534 |
| 2004/0143194 A1 * | 7/2004 | Kihara et al. ................ 600/534 |
| 2004/0249299 A1 * | 12/2004 | Cobb ........................... 600/529 |
| 2005/0054941 A1 | 3/2005 | Ting et al. |
| 2005/0228234 A1 | 10/2005 | Yang |
| 2006/0178591 A1 * | 8/2006 | Hempfling ................... 600/529 |

* cited by examiner

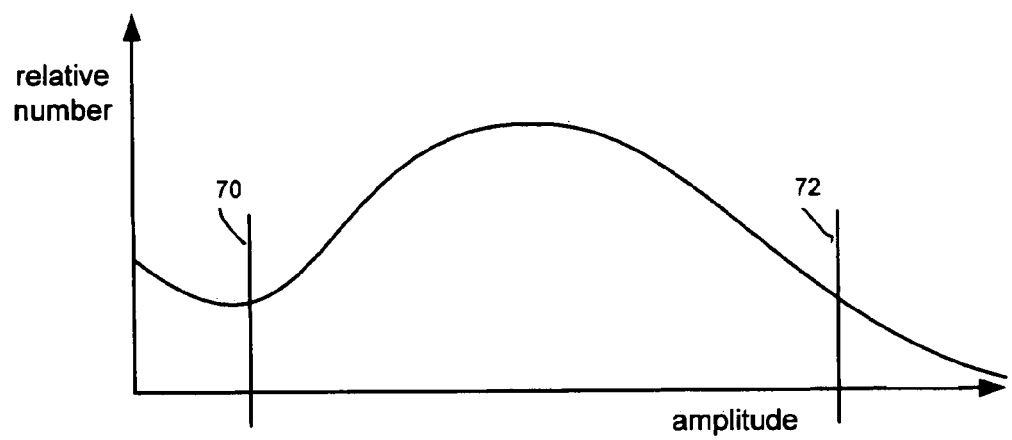
FIG. 3C
normal respiration
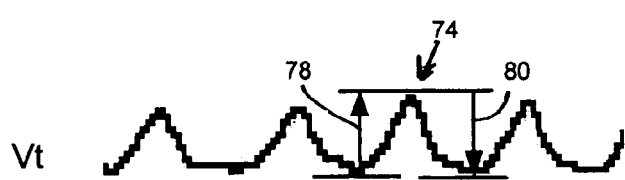
FIG. 4A
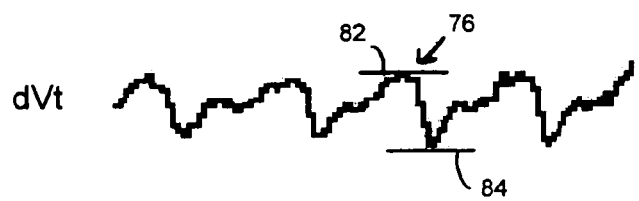

SYSTEMS AND METHODS FOR RESPIRATORY EVENT DETECTION

Priority and benefit is claimed from U.S. provisional patent application Ser. No. 60/461,738, which was filed Apr. 10, 2003 by Sackner Inman, and Wilhelm and titled "Systems and Methods for Respiratory Event Detection", and from U.S. provisional patent application Ser. No. 60/506,904, which was filed Sep. 26, 2003 by Sackner Coyle, Keenan Inman, and Wilhelm and titled "Systems and Methods for Respiratory Event Detection". These two patent applications are incorporated herein, in their entirety, by reference for all purposes.

1. FIELD OF THE INVENTION

The present invention provides systems and methods for improved processing of data from ambulatory recordings of physiological parameters, in particular from inductive plethysmographic recordings of cardio-respiratory parameters; also provided are systems methods for detection of intermittent physiological events, such as coughs and sighs, that are enabled by the improved processing.

2. BACKGROUND

Continuous ambulatory monitoring of physiological parameters can expand our understanding of the basis of clinically-relevant symptoms of daily life and how their experience is shaped by a subject's concurrent activities and behaviors. Although promising new, technologies have been developed, ambulatory monitoring data are often difficult to interpret. A major problem is that physical activity is not controlled as it is in the laboratory or clinic; if unknown, it can lead to a confusion of ordinary exercise-induced physiological changes with disease indications. Thus, a clinically-relevant ambulatory monitoring system advantageously should register motor activity to provide an evaluative context that can enable a clinician to judge whether any abnormal value (e.g., in the ECG or respiratory pattern) can be attributed to physical exercise or represent physiological dysregulation. A diary, either paper-and-pencil or electronic in which monitored subjects may record their activity, posture, and location, can help with further clinical interpretation by providing more contextual information. However, diaries are unsatisfactory when used alone because of often documented inaccuracy in reporting changes in location and activity levels.

Speech is an important activity that can confound ambulatory monitoring, especially of respiration. Speaking episodes, one of the most frequent types of physical activity and behavior, can alter a variety of physiological systems in addition to pulmonary functioning. For example, heart rate typically increases with conversational speaking from 5 to 10 beats per min. Heart rate increases can be much higher in socially demanding situations. Auditory recording with a microphone has been used to quantify speech activity, but is limited because it also picks up sounds other than the voice of the person monitored, like ambient sounds and the speech of others. A throat microphone is more selective, but wearing it over extended periods is inconvenient and attracts undesirable social attention to the monitored subject.

Inductive plethysmography (IP) is a scientifically and clinically accepted gold standard for unobtrusive respiratory monitoring of cardio-respiratory function, and has been used widely in clinical and research settings. For respiration, this technique approximates the amount of air moved by the respiratory system by measuring the expansion and contraction of both the rib cage and abdominal compartments, using IP sensors consisting of sinusoidal arrangements of electrical wires embedded in elastic bands. A high frequency, low voltage oscillating current is passed through the wires to generate a magnetic field needed to measure the self-inductance of the coils, which is proportional to the cross-sectional area surrounded by the band. After calibration of the rib cage and abdominal bands, a weighted sum of the two signals corresponds or is proportional to tidal volume.

Thus there is a need in the art for improved systems and methods for registering or detecting physical activity, especially speech, and for utilizing activity information to provide improved and more reliable interpretation of ambulatory monitoring data. Such systems should be directly applicable to ambulatory monitoring by inductive plethysmography.

Citation or identification of any reference in this section or any section of this application shall not be construed that such reference is available as prior art to the present invention.

3. SUMMARY

The objects of the present invention are to overcome deficiencies in the prior art by providing systems and methods for improved processing of data from ambulatory recordings of parameters sufficient to characterize a lung model, preferably, a two compartment lung model from which respiratory parameters, for example, lung volumes (Vt), may be derived. Accordingly, preferred input parameters characterize rib cage (RC) volume and abdominal (AB) volume such as by providing an indication of the cross-sectional area, circumference, or radius (or similar geometric variable) of a portion of the RC and of the AB. Such preferred parameters are preferably determined by respiratory plethysmography based on electrical, optical, or other technologies using sensors foxed relative to the torso of a monitored subject such as by being incorporated in a garment.

Although respiratory inductive plethysmography (RIP) is the preferred measurement technology, the systems and methods of this invention are readily adapted to other sensor technologies. Such sensors technologies include, for example, body impedance sensors; mercury-containing silastic strain gauges, bellows pneumographs, volume pneumographs, differential linear transformers, inductive transducers of body circumference, magnetometers sensing body diameters, piezoelectric transducers measuring local movements, movement analysis by optical reflection, and so forth. Further, the present systems and methods also readily adapted to sensor technologies generating a plurality of signals reflecting a plurality of parameters of body circumferences, diameters, distances, and movements that together at least provide indicia of a two-compartment breathing model and/or improvements thereto such as shape changes of the rib cage and abdomen. Additionally, these methods may be applied to the signals directed reflective of airflow, such as signals generated by the various air flow monitors including thermocouples, thermistors, end-tidal carbon dioxide sensors, nasal pressure and flow cannulas, breathing masks, sensors of differential pressures in airflow, and so forth.

Further objects of the present invention are to overcome deficiencies in the prior art by providing systems and methods for improved processing of physiologic data reflecting respiration such as, preferably, the time course of lung volume, or the tidal volumes of sequential breaths, of the like, in order to detect physiological events, such as apneas, hypopneas, coughs, sighs, and the like. Input data for these further systems and methods may be derived from many sources and many sensor technologies. Preferably, this input data derives from ambulatory recordings sufficient to characterize a two compartment lung or breathing model.

Although this invention is described herein primarily in its application to ambulatory recording, it should be appreciated that part or all of its systems and methods are applicable in other settings, such as in the laboratory, the clinic, or the hospital.

Certain embodiments are summarized in the appended claims.

Various references, including patents and printed publications, are cited throughout this application. All such cited references are incorporated herein, in their entirety, by reference for all purposes.

4. BRIEF DESCRIPTION OF THE DRAWINGS

The present invention may be understood more fully by reference to the following detailed description of the preferred embodiment of the present invention, illustrative examples of specific embodiments of the invention and the appended figures in which.

Figure 3A:
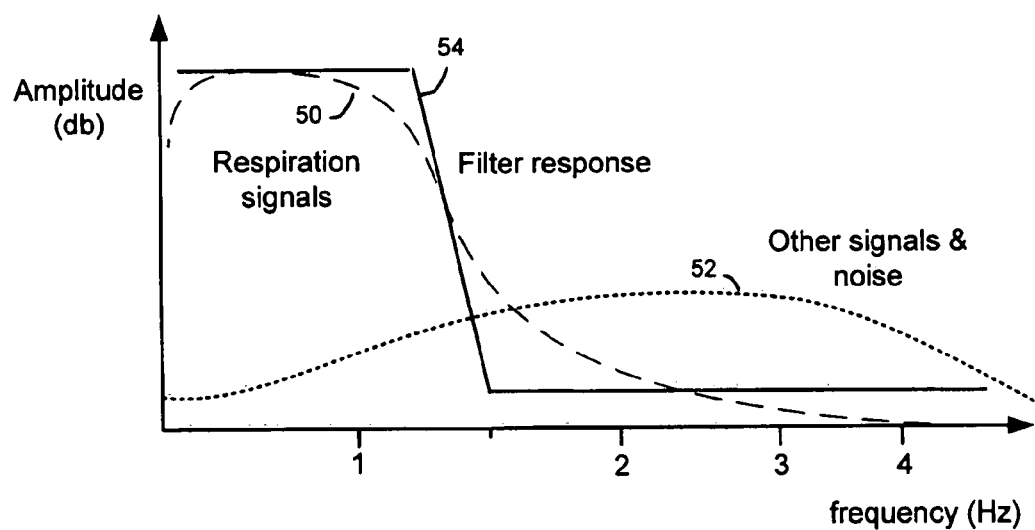
Figure 3B:
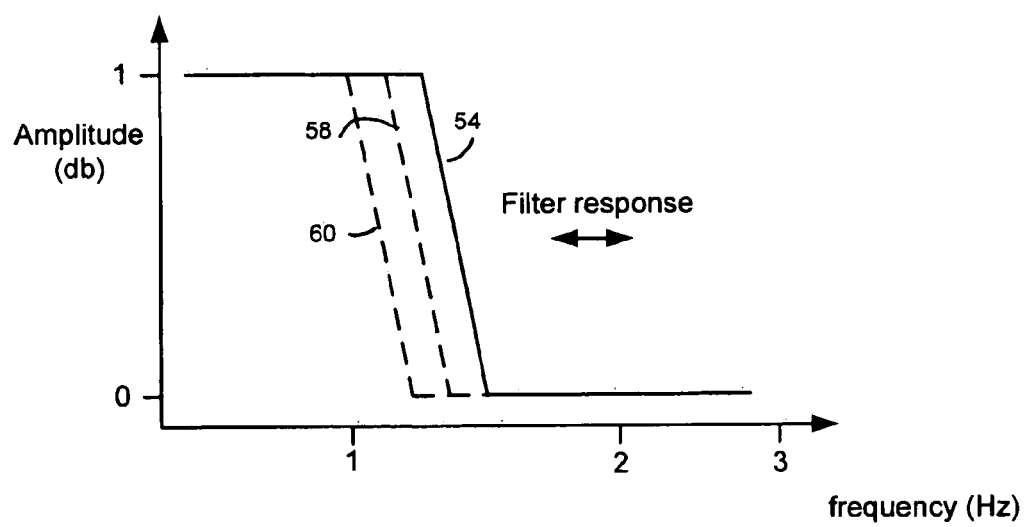
Figure 4B:
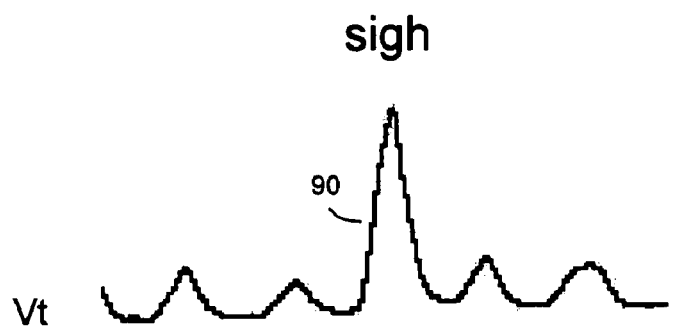
Figure 4B:
Figure 4C:
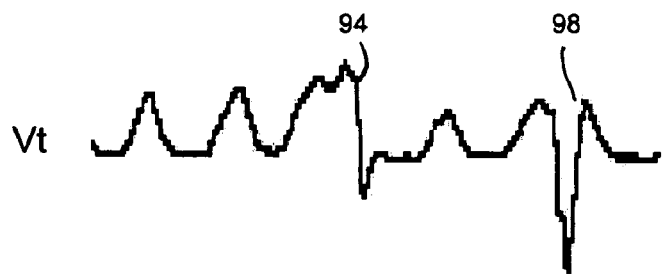
Figure 4C:
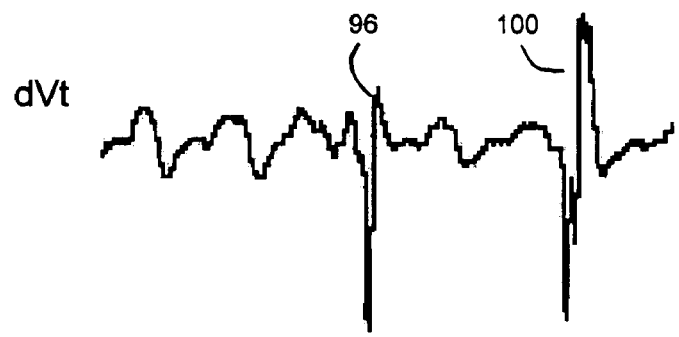
Figure 5A:
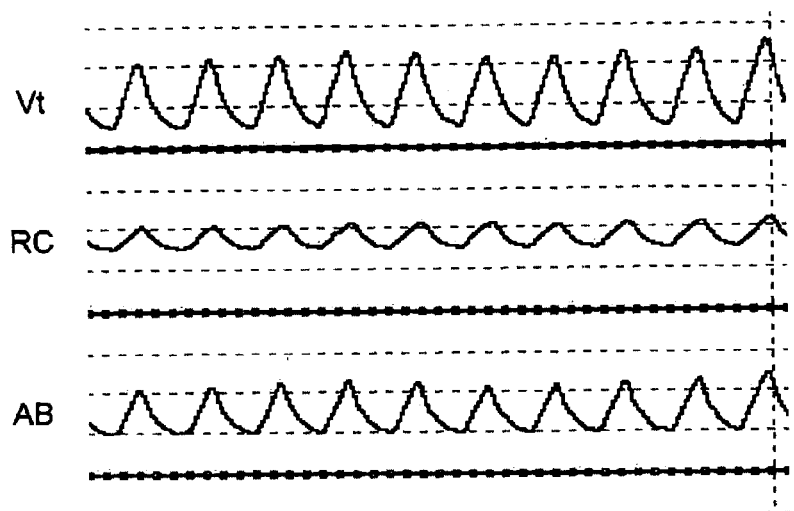
Figure 5B:
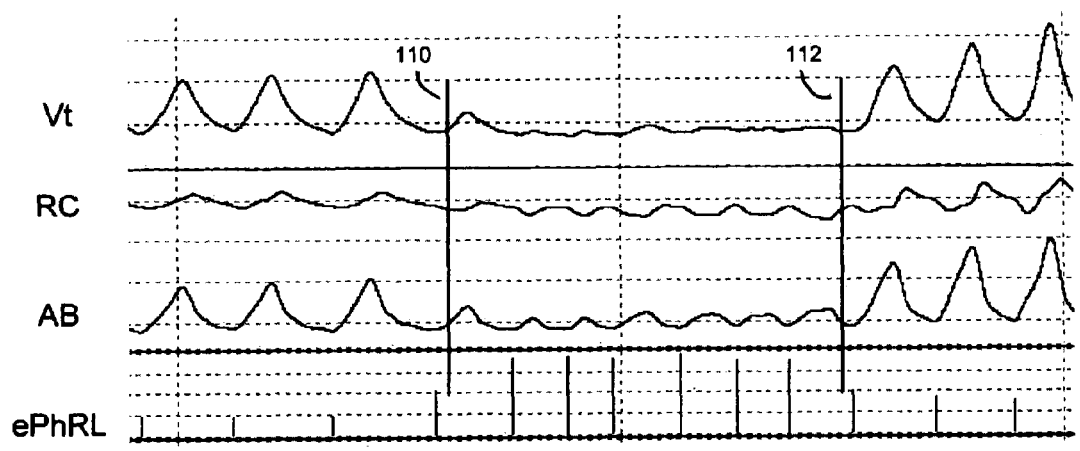
Figure 6:
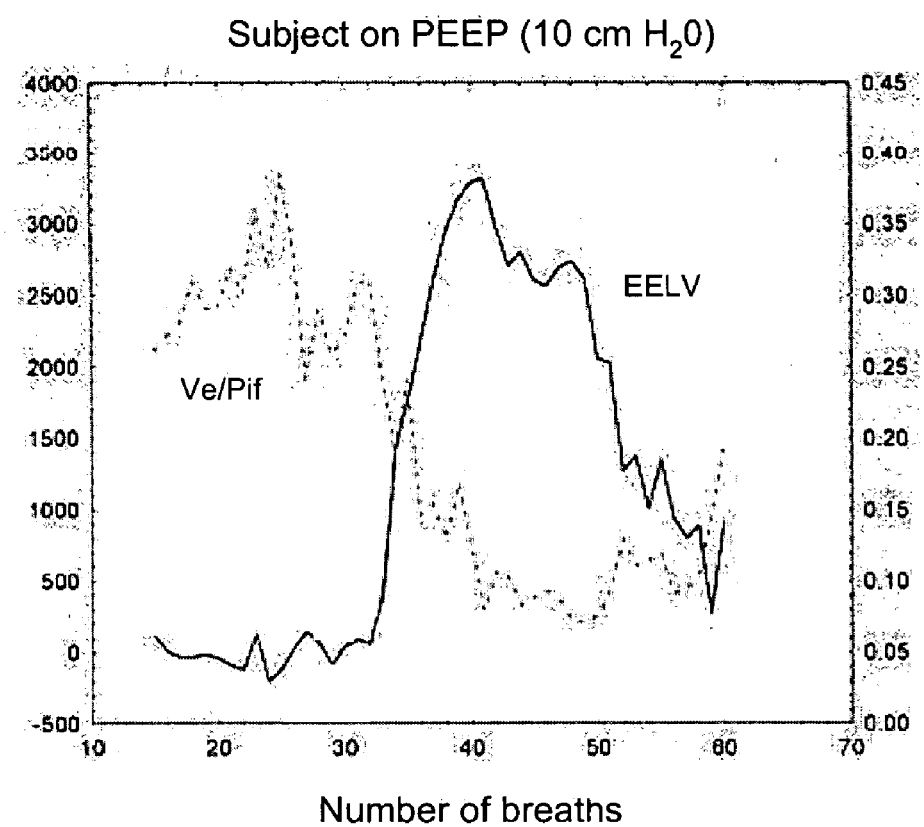
Figure 7:
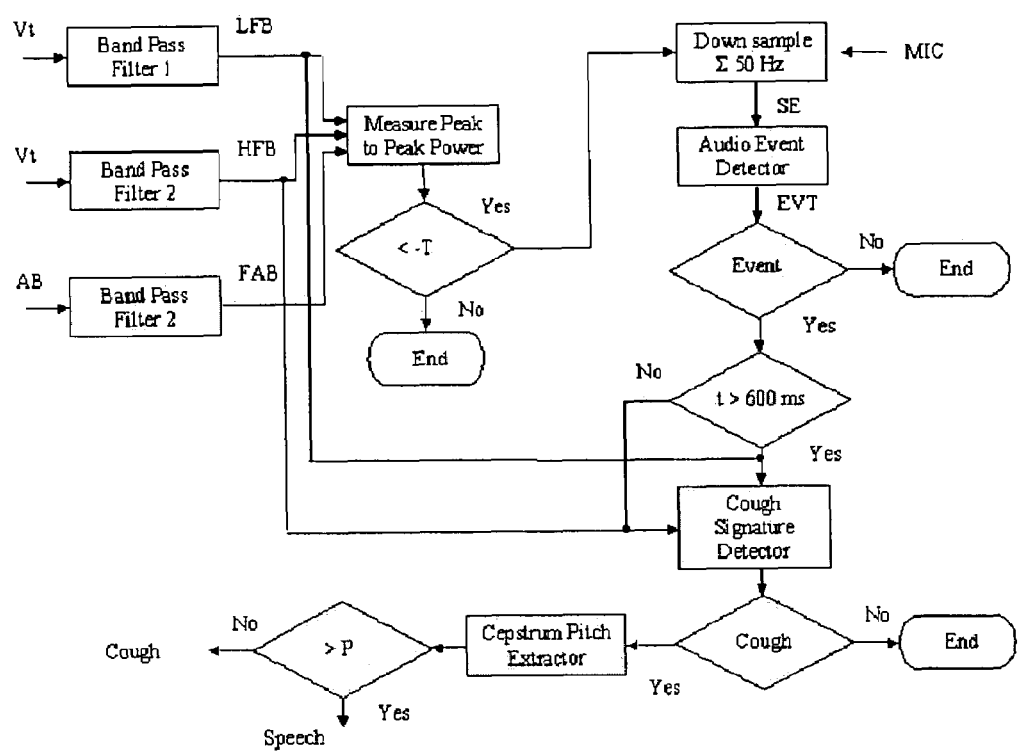
Figure 8A:
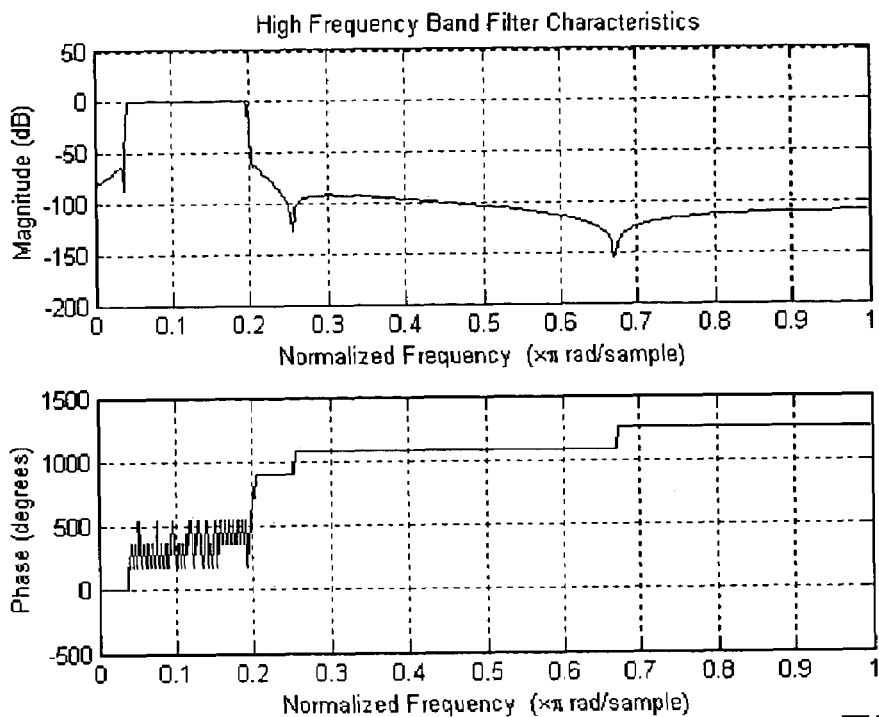
Figure 8B:
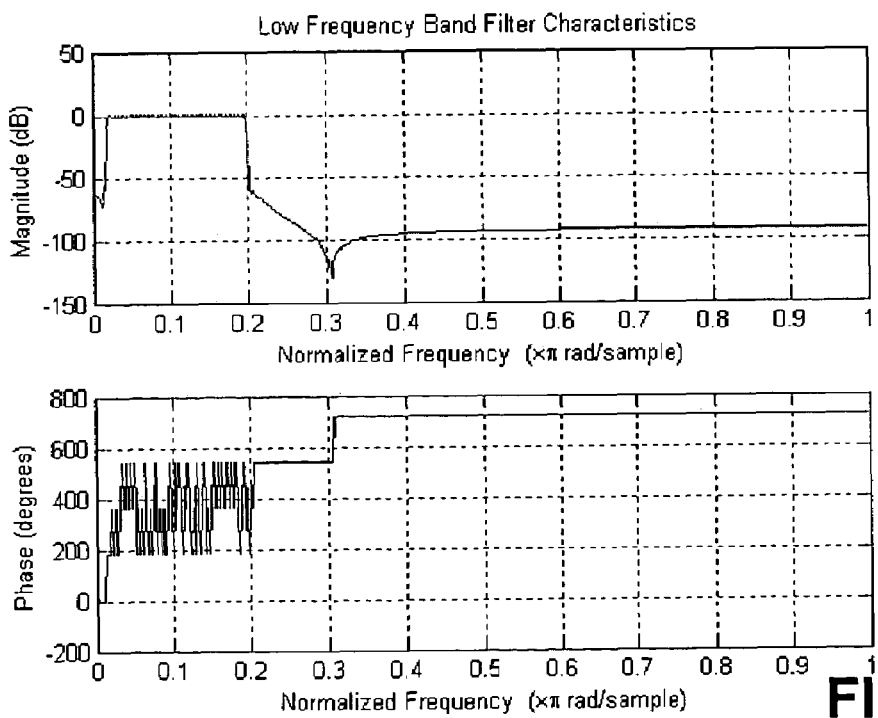
Figure 9:
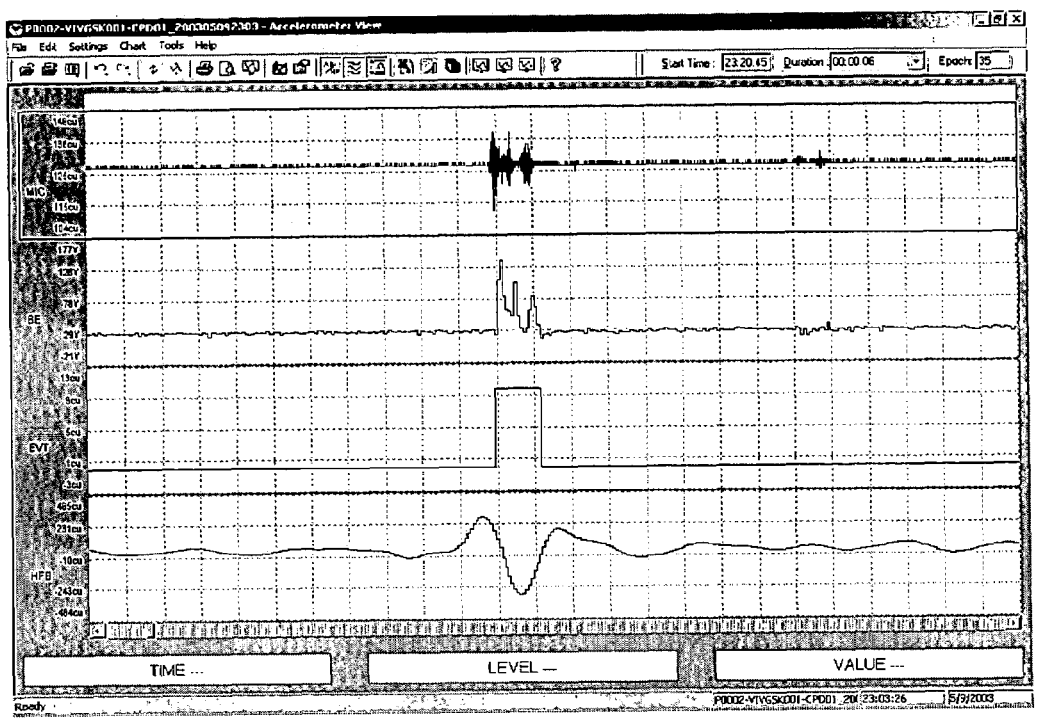
Figure 10:
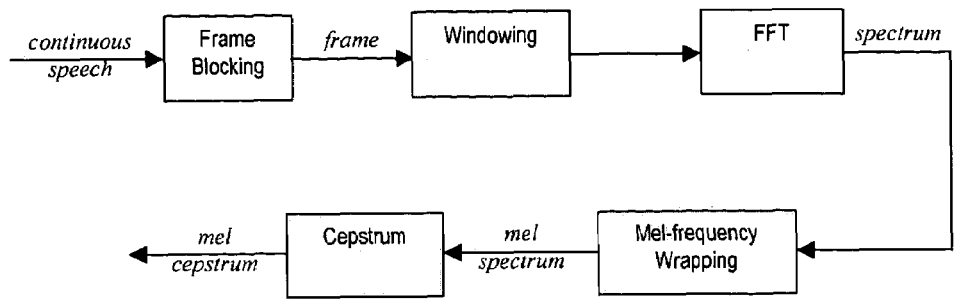
Figure 12A:
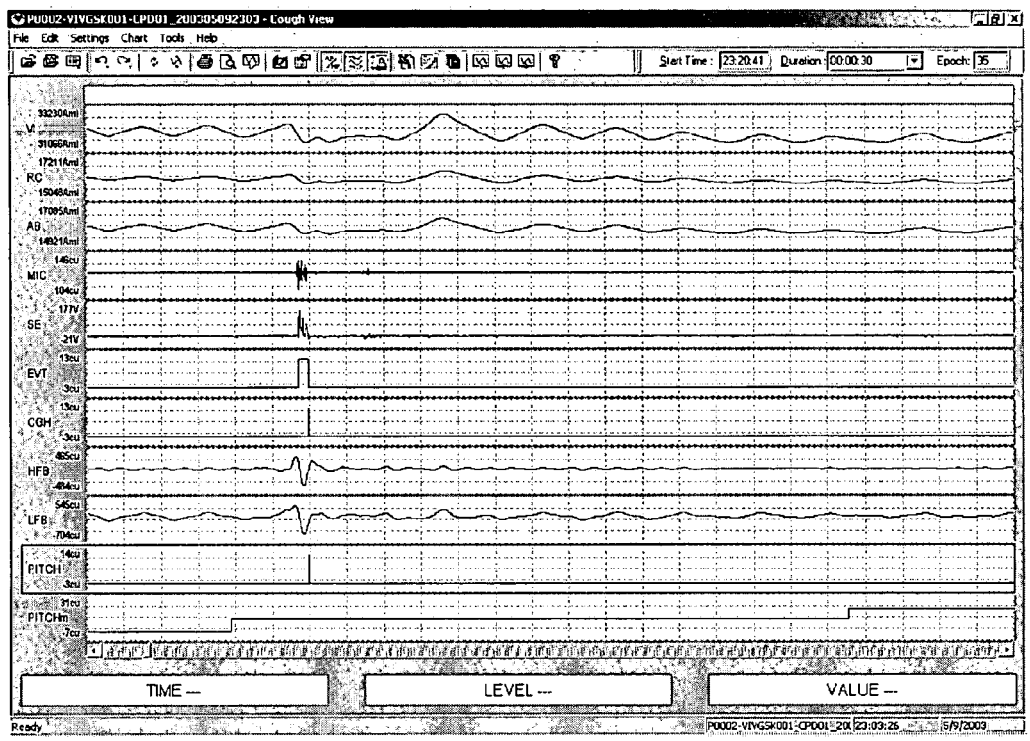
Figure 12B:
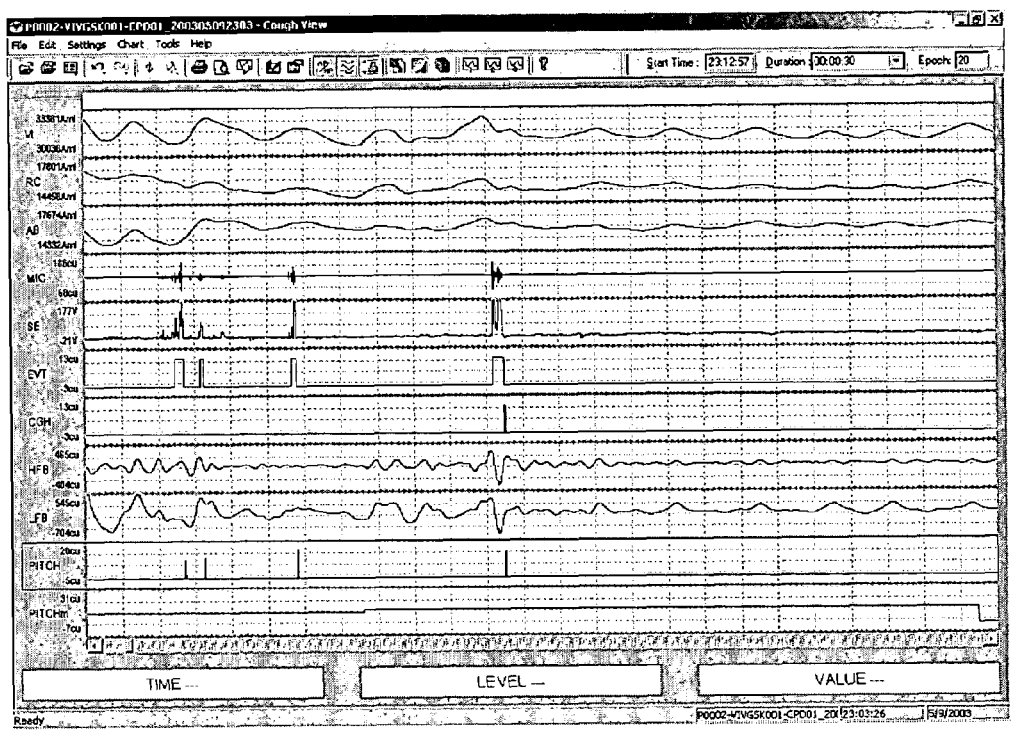
Figure 13A:
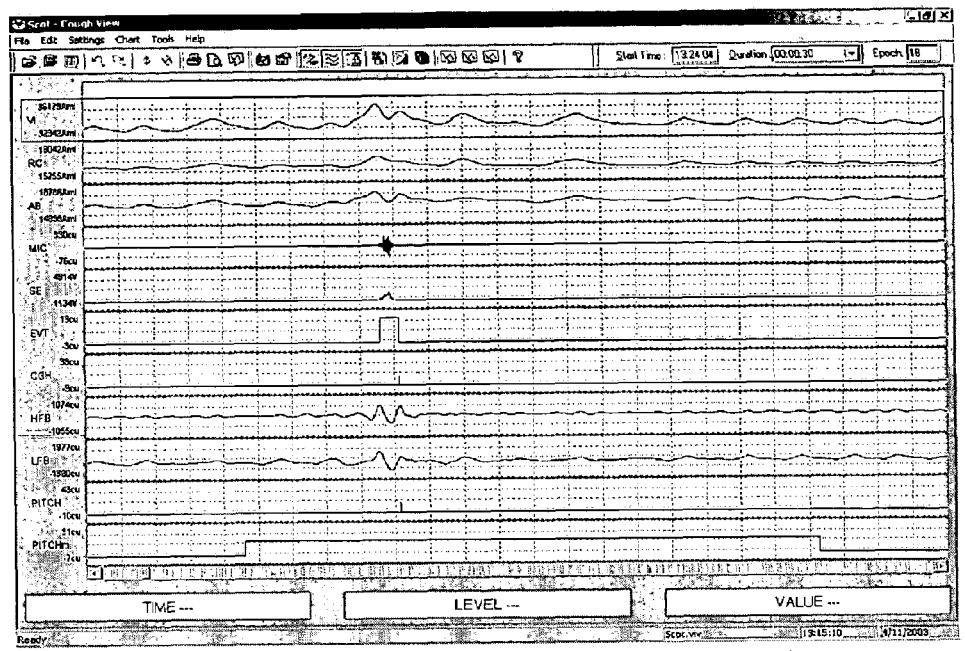
Figure 13B:
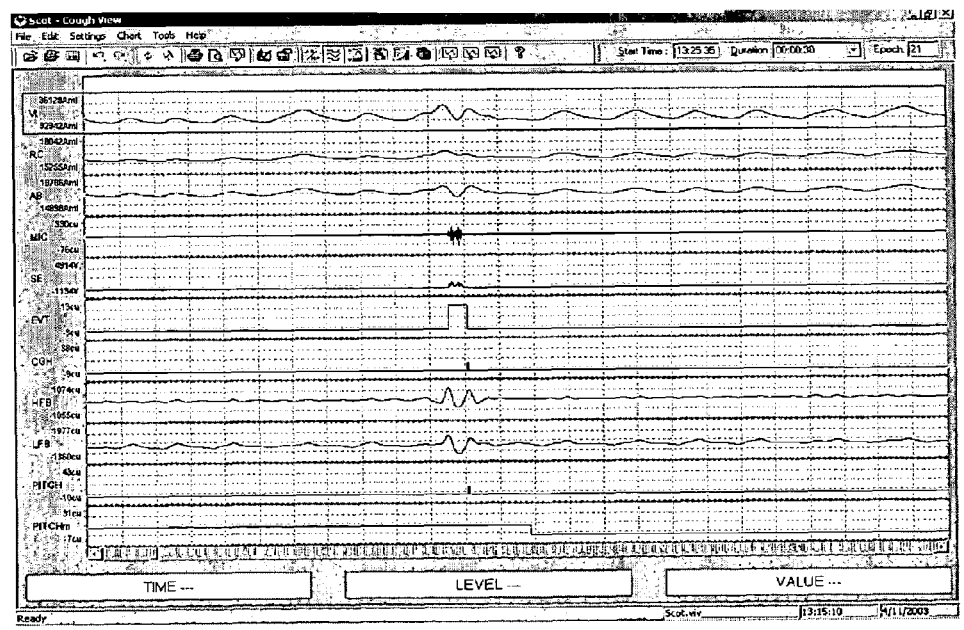

FIGS. 3A-C illustrate exemplary signal distributions and filter characteristics;

FIG. 4A-C illustrate exemplary respiratory signals;

FIG. 5A-B illustrate further exemplary respiratory signals;

FIG. 6 illustrates the effects of pulmonary hyperventilation;

FIG. 7 illustrates alternative methods of cough detection;

FIGS. 8A-B illustrate preferred digital filter responses;

FIG. 9 illustrates exemplary data recorded during a cough;

FIG. 10 illustrates preferred methods of pitch determination in audio signals;

FIGS. 11A-D illustrate pitch determination in a exemplary sound signal;

FIGS. 12A-B illustrate exemplary coughs of a COPD patient;

FIGS. 13A-B illustrate exemplary coughs of a CF patient; and

Figure 14A:
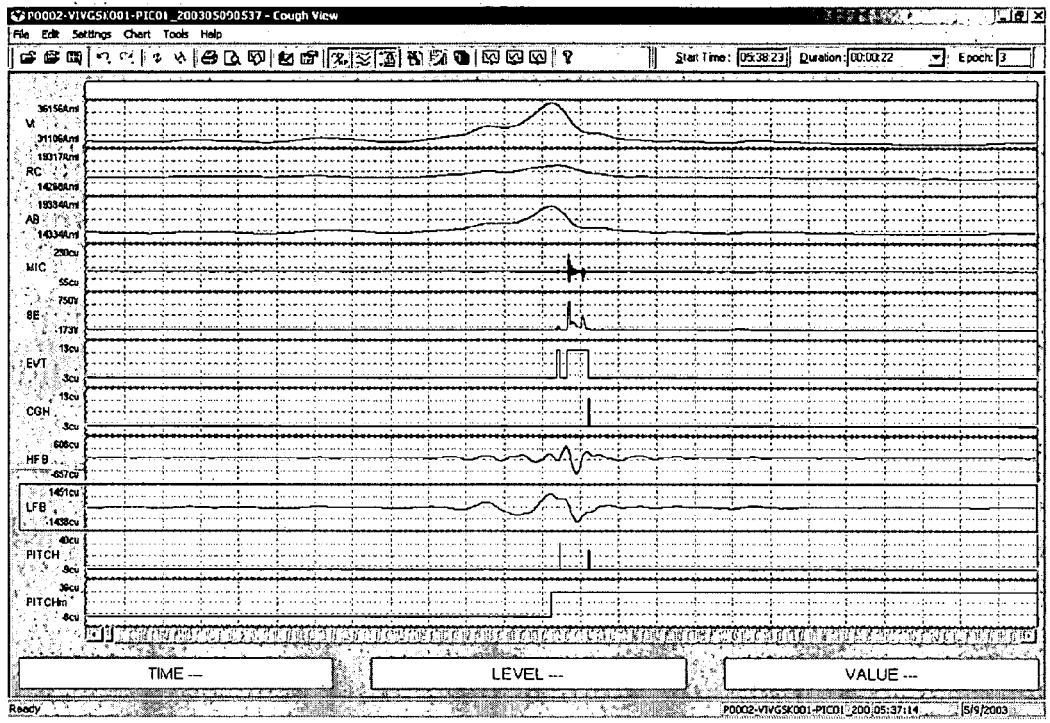
Figure 14B:
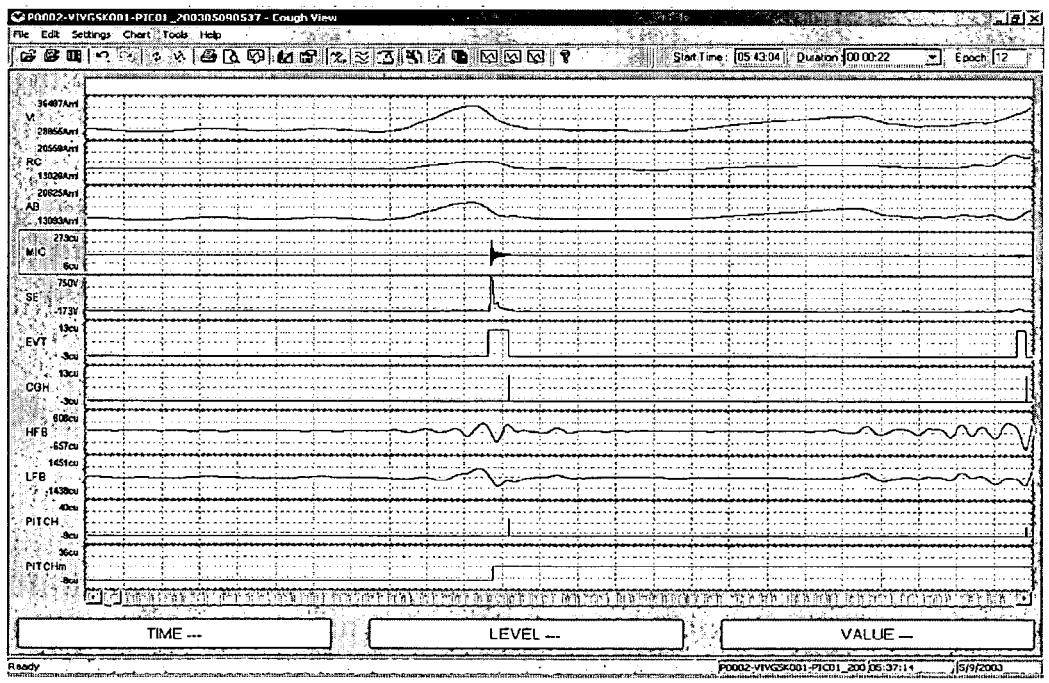

FIGS. 14A-B illustrate exemplary coughs of a PlC patient.

5. DETAILED DESCRIPTION

Although this invention is described below with primary reference to input data derived from preferred respiratory inductive plethysmographic (RIP) technologies, it will be understood that the systems and methods described are useful with data derived from other sensor technologies. For example, the preliminary signal processing may be applied to data characterizing a two compartment breathing model however derived. Also, determination of respiratory events from the time course (continuous or discrete) of indicia of lung volumes is useful however the requisite input data is derived.

Further, this invention has several features and aspects which are primarily described below as components of a single system and method. It will also be understood that this invention is not limited to such single embodiments, but also includes other embodiments having other combinations and sub-combinations of these features and aspects with independent usefulness. Also, although the description and figures of this invention's systems and methods are in a certain order, this order will be understood not to be unique or limiting. The steps, features, and aspects may be practiced on other temporal orders consistent with the described data dependencies.

5.1 Preferred Plethysomographic System

By way of brief background, respiratory plethysmography (RP) and respiratory inductive plethysmography (RIP) are next described, and this is followed by a brief description of a preferred implementation of this sensor technology. "Plethysmography" is used herein to mean determination of the volume of an organ due to, for example, changes in the volume of an included fluid such as air in the lungs, blood in a vessel, and so forth.

A. Rip Technology Summary

RP determines indicia reflecting moment-by-moment volumes that are sufficient to characterize respiratory function, for example, the areas (diameters, radii, etc.) of one or more cross-sectional planes through a subject's rib cage (RC) and one or more cross-sectional planes through a subject's abdomen (AB). From such indicia with reference to a two compartment model of respiration, lung volumes, cardiac volumes, and the like, man be determined.

RIP determines such indicia by measuring the self-inductance of a wire loop, which depends in large part on the loop's enclosed cross-sectional area, positioned around the subject's body in the cross-sectional planes of interest. Preferably, loop self-inductance is measured by including the loop in an oscillator, and measuring the oscillator frequency. See, for example, U.S. application Ser. No. 09/836, 384, filed Apr. 17, 2001 (an improved ambulatory inductive plethysmographic system); U.S. Pat. No. 6,047,203, issued Apr. 4, 2000 (an ambulatory inductive plethysmographic system including a sensor garment); U.S. Pat. No. 6,341, 504, issued Jan. 29, 2002 (stretchable conductive fabric for inductive-plethysmographic sensors); U.S. Pat. No. 4,807, 640, issued Feb. 28, 1989 (stretchable inductive-plethysmographic transducer); U.S. Pat. No. 5,331,968, issued Jul. 26, 1994 (inductive-plethysmographic sensors and circuitry); and U.S. Pat. No. 5,301,678, issued Apr. 12, 1994 (stretchable inductive-plethysmographic transducer).

Specifically, for respiratory measurements, signals obtained from RC and AB RIP loops is advantageously filtered, smoothed, and calibrated to derive indicia reflecting moment-by-moment lung volumes. See, for example, U.S. Pat. No. 5,159,935, issued Nov. 3, 1992 (measurements of individual lung functions); U.S. Pat. No. 4,815,473, issued Mar. 28, 1989 (methods for monitoring respiration volumes); and U.S. Pat. No. 4,308,872, issued Jan. 5, 1982 (methods for monitoring respiration volumes); U.S. Pat. No. 6,413,225, issued Jul. 2, 2002 (methods for calibrating inductive-plethysmographic breathing monitors); U.S. Pat. No. 4,834,109, issued May 30, 1989 (methods for calibrating inductive-plethysmographic breathing monitors); and U.S. Pat. No. 4,373,534, issued Feb. 15, 1983 (methods for calibrating inductive-plethysmographic breathing monitors).

Additionally, inductive plethysmography can be used to determine other physiological indicia. For example, from mid-thoracic sensor loops data may be extracted reflecting moment-by-moment cardiac volumes, cardiac output, and ventricular wall motion, and from sensor loops about the extremities or the neck, data reflecting arterial and venous pulses may be extracted. See, for example, U.S. application Ser. No. 10/107,078, filed Mar. 26, 2002 (signal processing techniques for extraction of ventricular volume signal); U.S. Pat. No. 5,178,151, issued Jan. 12, 1993 (methods for inductive-plethysmographic measurement of cardiac output); U.S. Pat. No. 5,040,540, issued Aug. 20, 1991 (inductive-plethysmographic measurement of central venous pressure); U.S. Pat. No. 4,986,277, issued Jan. 22, 1991 (inductive-plethysmographic measurement of central venous pressure); U.S. Pat. No. 4,456,015, issued Jun. 26, 1984 (measurement of neck volume changes); and U.S. Pat. No. 4,452,252, issued Jun. 5, 1984 (determining cardiac parameters from neck and mouth volume measurements).

B. Preferred Rip System

Figure 1:
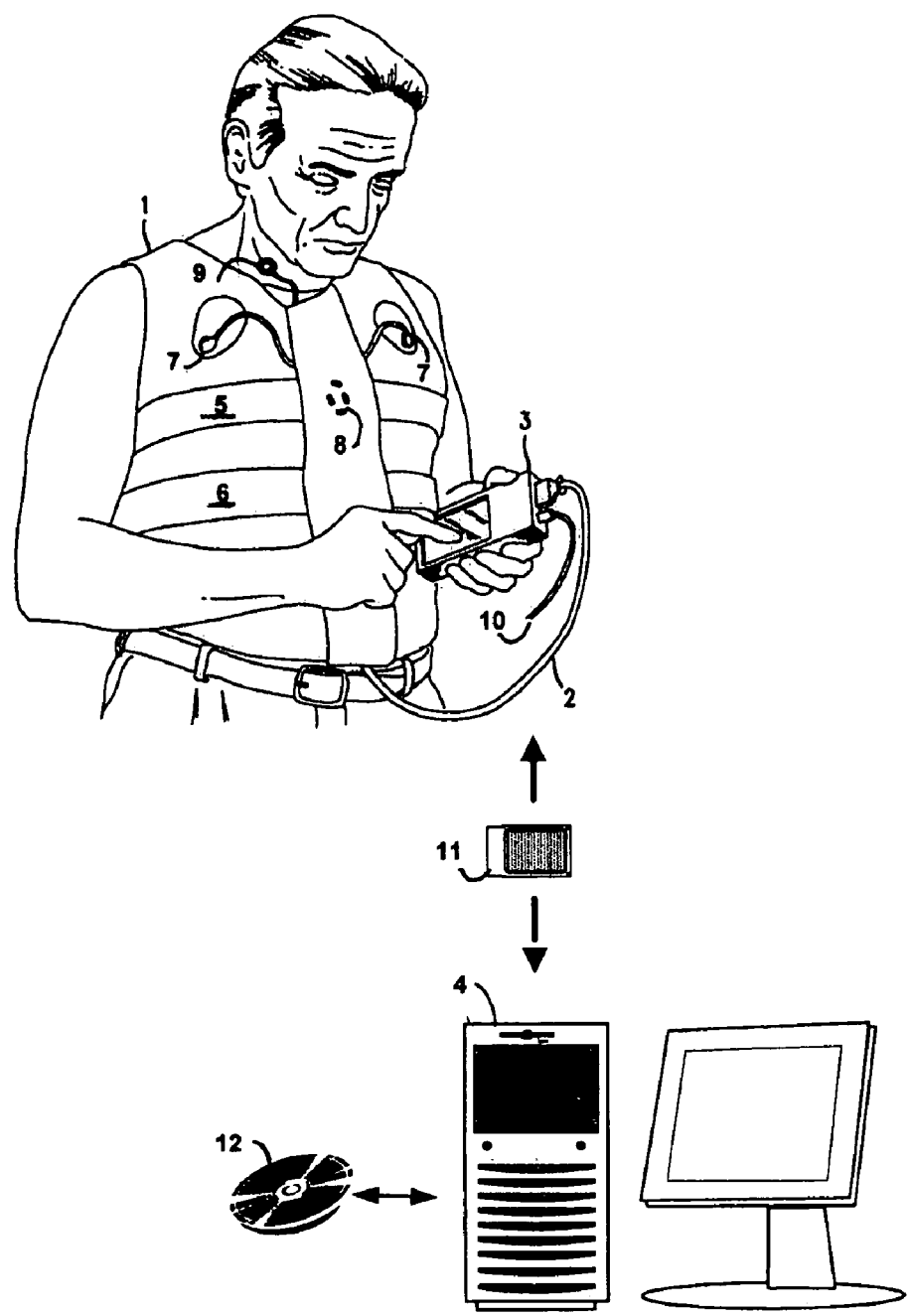
FIG. 1 illustrates a preferred plethysmographic recording and analysis system.

FIG. 1 illustrates a preferred (but not limiting) RIP system which is suitable for measuring signal that are analyzed by the systems and methods of this invention. This preferred system includes garment 1, data recording unit 3, and analysis computer 4 configured with an analysis software package for offline and interactive signal analysis, display, and report generation. The preferred garment illustrated (also referred to herein as a "shirt") is made of washable, reusable stretchable material that fits sufficiently snugly to expand and contract with a subject's body and includes one or more embedded RIP sensor bands. The sensors configured conductive wire loops positioned around a body cross-section and configured for expansion and contraction by, for example, having a sinusoidal-type arrangement. Inductance of the RIP sensors are converted to electrical signals, typically frequency signals, using methods known in the electrical and electronic arts.

The sensors are embedded in the shirt to ensure their correct and durable placement relative to a subject's torso. For measuring respiration, two sensors are preferred: sensor 5 at the level of the rib cage: and sensor 6 at the level of the abdomen. For measuring cardiac parameters, a mid-thoracic RIP sensor (not illustrated) positioned just below the level of the xiphoid process is preferred. A shirt may include or attach additional types of sensors, including: electrocardiogram sensors 7; one or more accelerometers and the like for sensing body posture and motion (exemplary accelerometer 8 illustrated as within the shirt and others not illustrated), microphone 9, a pulse oximeter (not illustrated), a capnograph, one or more EEG electrodes, and the like. In the hospital, clinic, or laboratory, other signals may derive from a wide range of physiological sensors. The illustrated RIP technology is the now preferred embodiment; future garment configurations and sensor packaging may contain, for example, additional RIP sensors and plethysmographic sensors of other technologies (for example, employing optical sensor or sensing Doppler shifts in electromagnetic or acoustic energy after interaction with a subject). and the methods to be described below are applicable to such data including additional sensors.

The illustrated shirt-mounted sensors may attach to the data recording unit via cable 2, and other peripheral diagnostic devices (not illustrated) may attached to the data recording unit by auxiliary cable 10. Alternatively, local wireless links, optical links, or links embedded in the short or its fabric may be used in place of discrete cables. Data storage unit 3 so preferably compact and lightweight so that it can be worn on a belt, put in a pocket, or embedded in the shirt. This unit stores sensor waveforms with sufficient accuracy and precision for full disclosure storage and off-line analysis, and/or may perform certain processing and analysis locally. Data is transferred to analysis computer 4 by removable, standardized memory cards 11 (for example, flash memory cards), or alternatively by wireless links, such as transmission using cell phone technologies. The data recording unit may include a touch screen for implementing a digital diary whose data may also be transferred to the analysis computer for correlation with the sensor readings.

The systems and methods of this invention are implemented by analysis software that is executed on analysis computer 4 (and optionally also in part in data unit 3). This software reads data from the memory card, or otherwise receives sensor data, and extracts and displays according to the methods of this invention a variety of physiological parameters, such as minute ventilation, tidal volume, respiratory rate, inspiratory flow rate, and so forth which characterized a subject's respiratory patterns. Analysis software package is advantageously controlled interactively by a user of an analysis computer. Also, this invention contemplates that the all of selected portions of the analysis software implementing this invention's methods may be made available as a program product which is transferred to analysis computers on a computer readable medium, such as CD-ROM 12.

Additionally, the analysis software advantageously processes signals from other sensors along with or in combination with the RIP signals. For example, pulse oximeter signals can provide concurrent arterial oxygen saturation information; accelerometer signals (and signals from similar sensors) can be processed to provide indicia of a subject's posture and activity. Posture and activity importantly provides a behavioral context for the concurrently measured cardio-pulmonary measurements.

5.2 Respiratory Signal Processing

Figure 2:
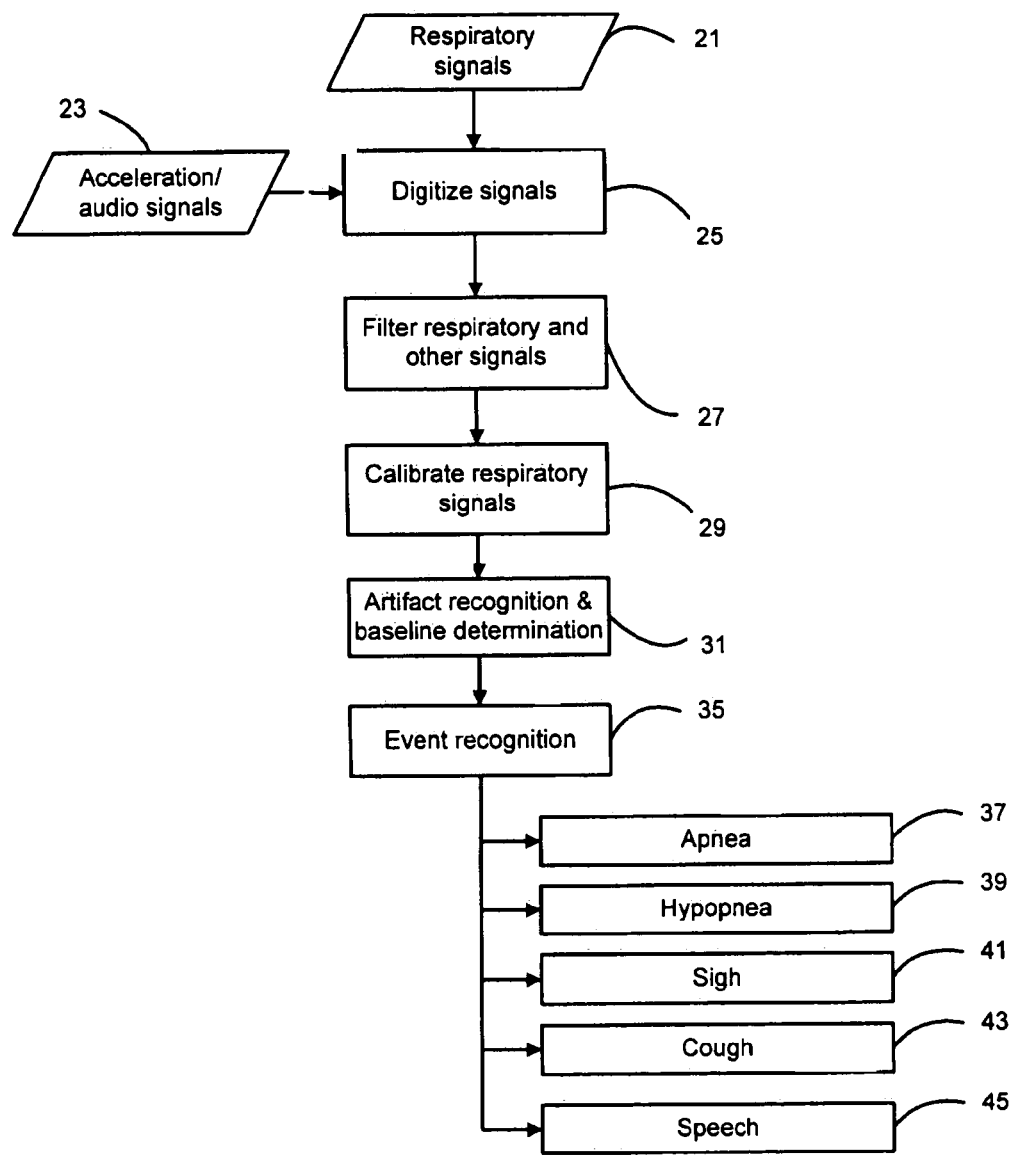
FIG. 2 illustrates preferred signal processing elements.

With reference to FIG. 2, preferred embodiments of the respiratory signal processing methods are now described. For simplicity and without limitation, headings are used to organize this description.

5.2.1 Input Signals

Requisite input signals provide parameters for non-invasively determining respiratory volumes in accordance with, preferably, a two component breathing model. See, e.g., chap 10 (Respiratory System) in Stern et al., *Psychophysiology Recording Second Edition*, Oxford University Press, Oxford, U.K. Briefly, the two compartment model conceptualizes lung volume a determined from the diameter of the rib cage (similar to a variably-sized cylinder) and the position of the diaphragm (similar to a piston in the cylinder). The position of the diaphragm is reflected by the volume of the abdomen whose relatively incompressible viscera are compressed by the diaphragm. Accordingly, in preferred embodiments, a pair of respiratory signals 21 reflecting RC and AB sizes are input from respiratory plethysmographic sensors (RP), such as the from the RIP technology sensors described previously. Alternatively, input signals may provide data for other breathing models which output Vt and/or Vol signals (described subsequently) or equivalents. Such output signals can be processed by the respiratory event recognition methods or this invention whether or not they arise from a two component model.

In other embodiments, a plurality of input signals may reflect torso dimensions, movements, or shapes and may be generated by other than IP or RIP technologies. For example, optic or fiber-optic based RP may be used as well as RIP. Also sensors reflecting several parameters of torso shape may be input to this invention. Such shape-reflecting signals can be processed into an RC and an AB signal for later use by, for example, linear combination with coefficients determined by well known regression methods that minimize the difference between such a linear combination and concurrent RP or RIP signals. Alternatively, such shape-reflecting signals can be processed directly into Vt signals (described subsequently) by, for example, an extension of the QDC methods, or into Vol signals (described subsequently) by, for example, linear regression methods applied to concurrent actual airflow information. Specifically in the case where such shape reflecting signals include an adequate plurality of indicia of distances defined on the surface of a subject's torso, such signals may be processed into a representation of the shape of the torso by methods known in the mathematical arts (specifically differential geometric methods). It is known that sufficient distances defined on a two dimensional surface (a metric) permit the shape of the surface to constructed in three dimensional space. For respiratory monitoring which involves only relatively small shape changes, this construction may be linearized around a shape of the resting torso. Accordingly, this geometric construction may be preferably avoided by linearly fitting the distance-reflecting signals to calibration air volumes by linear statistical model building methods.

Additional signals from one or more accelerometers, pulse oximeters, and microphones are advantageously processed along with the respiratory signals. Signals 23 from one or more accelerometers (8 in FIG. 1) positioned on a subject, for example, mounted on the torso, or on the leg, or on the foot (e.g., in a shoe) provide indicia of subject posture and motion or activity. Such information can provide a behavioral context of concurrent physiological data and (as subsequently described) can be used to filter or adaptively filter motion artifacts from RP signals. A microphone, such as a neck microphone (9 in FIG. 1) mounted to pick up a subject's vocalizations with minimal interference from ambient sound, can be used to determine the present of speech and to assist in discriminating coughs, sighs, and other respiratory events. Other optional sensors may provide additional information relevant to respiratory interpretation or processing.

5.2.2 Input Signal Digitization

The first steps in signal processing are signal digitization 25 and filtering 27. The following description follows the preferred sequence of steps, in which analog-domain signals are first digitized 25 and then the digitized signals filtered 27 according to known digital-filtering techniques. Less preferably, signals may be entirely filtered in the analog-domain and then digitized. However, even in the preferred sequence of steps, it is understood that a preliminary explicit or implicit step of analog filtering is performed so that the analog signals to be digitized have no components with frequencies greater than one-half the sampling rate (Nyquist condition).

Preferably, raw analog signals are digitized either by shirt-mounted electronics or by electronics in the data storage unit for recording and transfer in digital form. Signals are quantized (A/D converted) with at least 8-bit and more preferably with 16-bit precision. If necessary, only respiration signals may be quantized at 16-bit with the other signals (accelerometer, microphone, and so forth) at 8-bit. Preferred sampling rates vary with the type of signal.

Analog signals generated from RIP sensors are normally digitized for processing at an approximately a 50 Hz sample rate (20 msec. sample time) so that actual signals up to 25 Hz and events down to 40 msec. duration are represented. For processing of higher frequency respiratory phenomena rates and for more accurate calculation of time derivatives of digitized signals, a sample rate up to 400 Hz (2.5 msec. sample time) may be used; alternatively sample rates as low as 30-40 Hz may be used to limit storage requirements in the portable data storage unit. These sampling rates are implemented, for example, as described in copending application Ser. No. 09/836,384, filed Apr. 17, 2001.

Accelerometer signals are preferably digitized at approximately 10 Hz (100 msec. sample time) (range 8-16 Hz) and can be quantified in "G's" of acceleration. For determination of sound quantity (intensity), microphone signals are preferably digitized at approximate 10 Hz and quantified in decibels, but for obtaining acoustic characteristics sufficient to distinguish speech, snoring, coughing, and so forth, sample rates from 1 kHz up to 10 kHz are preferable.

5.2.3 Input Signal Filtering

Signal filtering 27, preferably digital, may be performed as signals are being measured and prior to their recording onto transferable memory cards. Alternatively, digitized but unfiltered signals may be recorded on the memory cards and then later filtered by software on the analysis computers.

Accelerometer signals, which in some embodiments are advantageously used to adaptively filter respiratory signals, are digitized and processed to provide indications of the subject's posture, and/or activity, and/or motion. Preferred processing filters the input signal into a low-pass component that is more sensitive to posture and/or position and a high-pass component that is more sensitive to activity and/or motion. The high-pass/low-pass band separation is preferably chosen at a frequency characteristic of postural changes (perhaps individualized for each subject), for example between 0.1 Hz and 1 Hz (preferably 0.4-0.6 Hz). Indicia of posture may then be determined from the low-pass filtered accelerometer signals. For example, the direction of gravitational acceleration observed by an accelerometer at the torso can discriminate between a sitting/standing position and a supine position from, while a thigh-mounted accelerometer can similarly discriminate between a sitting/supine position and a standing position. Thus, signals from garment-mounted and thigh-mounted accelerometers can be combined to provide indicia of supine, sitting, or standing positions. Also, indicia of activity or motion can be determined from the high-pass filtered signals. For example, activity intensity is reflected by the total energy in the high-pass signal. Rate or type of activity is reflected in the modal frequency component present in the high-pass signal. Further, foot or shoe mounted accelerometers can provide indicia of forces generated in walking or running.

RC and AB signals measured by means of RP or RIP of course reflect respiration, and may also contain components reflecting cardiac activity, activity or motion induced artifacts, and noise. FIG. 3A schematically (not to scale) illustrates the spectrum discovered to be generated by RC and AB. First, respiratory signals 50 have generally moderate amplitudes with fundamental frequencies of about 0.2-0.5 Hz (14-30 breath/min) and harmonics extending to about 1.0-1.5 Hz. Cardiac signals, included in signals 52, generally amplitudes no more that 10-20% of respiratory amplitudes with have fundamental frequencies of 1-2 Hz (60-120 beats/min (but occasionally low 0.75 Hz or 45 beats/min) and harmonics to 3 Hz and higher. Especially ambulatory monitoring, motion artifacts are usually present. These artifacts, also included in signals 52, have widely varying amplitudes and frequency spectra, but for many common motions, have modal frequencies around 1-2 Hz with higher harmonics. Finally, noise from other sources, including the that intrinsic to the sensors and that introduced by the signal processing, generally has a low amplitude with flat spectrum in the range of interest.

Consequently, preferred embodiments filter RP or RIP signals in order to limit the cardiac, motion, and noise components signals while retaining the respiratory components and their harmonics for later processing. In one embodiment, a single low pass filter is applied to the RC and AB signals chosen to best separate the respiratory components from non-respiratory components in general, or for a population of subjects, of individualized for a single subject. FIG. 3A schematically illustrates an ideal such low-pass linear filter 54 with a generally frequency response: a pass band from 0.0 Hz to approximately 1.3 Hz; a roll off band of increasing attenuation from approximately 1.3 Hz to approximately 1.5 Hz; and a stop band above approximately 1.5 Hz. This and other digital filter of this invention, as a finite impulse response (FIR) filter with weight coefficients chosen as known in the art. See, e.g., Smith, $2^{nd}$ ed. 1999, *The Scientist and Engineer's Guide to Digital Signal Processing*, California Technical Publishing, San Diego, Calif. Such FIR filters may have from 100 coefficients, up to 250, and up to 1,000 or more coefficients as needed.

In further embodiments, RP or RIP signals filters that adjust or adapt to measurable characteristics of the non-respiratory signals have been found to lead to improved separation of respiratory from non-respiratory signals, especially in ambulatory contexts. In one such further "open-loop" type embodiment, one of a plurality of filters with different pass bands (or a single filter with an adjustable pass band) is selected moment-by-moment in dependence on motion or activity characteristics determined from accelerometer signals. Because motion artifacts have been found to generally extend to lower frequencies as motion and activity become more intense, such an embodiment can select filters with shorter (longer) pass bands when motion or activity intensity increases (decreases). Motion activity may be determined as, for example, the root mean square (RMS) average of recent filtered accelerometer signals.

FIG. 3B schematically illustrates one such embodiment. Here, filter characteristic 54 (similar characteristic 54 in FIG. 3A) is selected when there is little or no subject motion; filter characteristic 58, having a roll-off band from approximately 1.1-1.2 Hz to 1.3-1.4 Hz, is selected when there is average subject motion; and with intense subject motion, filter characteristic 60 having a roll-off band from approximately 0.9 Hz to 1.1 Hz, is selected. For certain subjects, Transient subject accelerations of less than approximately 0.1-0.2 g (acceleration of gravity) indicate little or not subject motion; transient accelerations of approximately 0.1-0.2 g to 0.3-0.5 g indicate average motion; and intense motion being indicated by transient accelerations over 0.3-0.5 g. This embodiment may be implemented by pre-computing three of more sets of filter weight coefficients, and then selecting from the coefficient sets according to (RMS) average amplitude of transient inputs from one or more accelerometers or other motion sensors.

Further adaptive embodiments may be constructed according to known principles of adaptive signal processing or signal estimation. An adaptively constructed embodiment for limiting non-respiratory signal components exploits on the correlation between filtered accelerometer data and signal components due to motion artifacts and on the correlation between cardiac pulse data from ECG or pulse oximeter signals and signal components due to cardiac components. Further, accelerometer signals are independent of the respiratory component of RP or RIP. Cardiac pulse data is similarly generally independent of the respiratory components, although some correlation may be due to respiration induced heart rate variability and amplitude. Motion artifacts may be limited by moment-by-moment adaptive processing or filtering (such filtering is generally digital) of RP or RIP (or other) signals using accelerometer signals as the noise signal reference, while cardiac signals may be generally limited using cardiac pulse data as the noise signal reference for further moment-by-moment adaptive processing or filtering. Adaptive interference limiting procedures are known in the art and are applicable both the single and multiple noise sources. Adaptive processing is preferably based on the LMS algorithm. See, e.g., Widrow et al., 1985, *Adaptive Signal Processing*, Pearson Education, Singapore, especially chapter 12 (Adaptive Interference Canceling).

It is often preferable to individualize filter and adaptation parameters for individual subjects. For example, such parameters for an athlete are likely to differ from those from for suffers of cardio-respiratory disease. Individual parameters may be determined from measurements during calibration periods when the subject instructed to undertake motion or activity of various selected intensities.

5.2.4 Respiratory Signal Calibration

The digitized RP signals that have preferably been filtered to limit non-respiratory components are next calibrated 29. This processing combines these signals, preferably processed outputs of RC and AB RIP sensors, into a further signal proportional to actual, moment-by-moment lung volumes (referred to herein as Vt). If data from more than two RP sensors are available, the prior digitization and filtering is preferably performed on all sensor signals, and the present calibration step extended in a readily apparent manner to determine a single signal proportional to lung volume from linear fits to all signals. This step and subsequent steps may be performed as sensor signals are received, or may be performed subsequently using signals.

According to two-compartment breathing models, the following linear combination results in a Vt signal proportional to moment-by-moment lung volume.

$$Vt = K*RC + AB$$

(alternatively, a general linear combination of RC and AB may be used). If measurements of actual respiratory air volumes (or flows) are available, Vt may be further calibrated into a signal closely reflective of actual lung volumes (referred to herein as Vol). Vol may be obtained by a linear scaling of the Vt signal.

$$Vol = M*Vt = M*K*RC + M*AB$$

M is a best fit to the ratio of these actual air volumes to the concurrent properly calibrated Vt signal. Actual air volume measurements may be made with measured with a calibrated re-breathing bag, preferred in ambulatory contexts, a spirometer, an integrated pneumotachograph, or the like. The subject is instructed to breath fully in and fully out, fully collapsing and then fully expanding the re-breathing bag (of, for example, 800 ml), for a certain number (for example, from 3-10) of breaths. Then M can be found from the known Vol and calibrated Vt signal by, for example, least squares fitting.

FIG. 5A illustrates exemplary RC and AB signals obtained from an actual subject monitored during steady breathing at rest. These signals are combined into the illustrated Vt signal using a K determined by the methods subsequently described. The Vt signal may be further scaled into a Vol signal (not illustrated). Much subsequent processing may be based on this Vt signal (and/or on the Vol signal) and respiratory parameters extracted from it.

A. Basic Calibration

K is preferably determined by an improved Quantitative Diagnostic Calibration (QDC) procedure. First, basic QDC is described followed by description of the improved procedure. See, e.g., U.S. Pat. Nos. 6,413,255 and 4,834,109, and also, Scharf (ed.), 1989, *Heart Lung Interactions in Health and Disease*, (ISBN 082477986X), pp. 676-678 (all incorporated be reference herein for all purposes).

Basic QDC determines or calibrates K from RC and AB signals measured with a subject breathing normally in behavioral conditions representative of the behavioral conditions that will prevail during subsequent monitoring, e.g., calibration during rest supine for a sleep study, or calibration during steady walking for an ambulatory study. Usually, the subject receives instruction on proper breathing and activity and on the calibration procedure; compliance may be confirmed by the RC and AB signals themselves or by concurrent accelerometer signals. Calibration measurements preferably includes at least 100 breaths (about 5 min); more preferably 250 breaths (about 10-15 min), and even more preferably, even more breaths (up to 1 hour and 1200 breaths). Longer calibration measurement periods are advantageous for improved accuracy especially in more active ambulatory settings. The signals should be relatively free or filtered to limit motion artifacts.

Next, all inspiratory and expiratory differences in the RC and AB signals are determined, that is the difference between each signal minimum and its immediately following signal maximum, and the difference between each signal maximum and its immediately following signal minimum. At least a set of 200 to 500 (or up to 2000) differences should be available. Finally, K is estimated as the ratio of the standard deviation (SD) of all inspiratory and expiratory differences measured in the AB signal to the SD of all inspiratory and expiratory differences measured in the all RC signal. Symbolically:

$$K = SD(AB \text{ inspiratory and expiratory differences}) / SD(RC \text{ inspiratory and expiratory differences})$$

B. Improved Calibration

Improved determination or calibration of K provides methods for improved elimination of outlier values present in the sets of inspiratory and expiratory differences measured in the RC and AB signals that are used for calibration purposes. Because these calibration methods depend on the pendulluft phenomenon, or internal respiration within each lung or between the two lungs, stringent elimination of outlying difference values from the sets of differences is advantageous so that the differences represent tidal respirations that are constant with little standard deviation. The inventors have discovered the following multi-step outlier elimination method.

In one embodiment of the improved method, the mean and standard deviation (SD) of the sets of all inspiratory and expiratory differences measured in the RC and AB signals are separately determined. Then, all difference values more than (for example)+/−3 SDs (first outliers) from the mean are discarded resulting in a first reduced sets of inspiratory and expiratory differences. Next, the mean and standard deviation (SD) of these first reduced sets of inspiratory and expiratory differences are determined, and all differences more than (for example)+/−2 SDs (second outliers) are discarded resulting in second reduced sets of RC and AB inspiratory and expiratory differences The mean and standard deviation (SD) of the second reduced sets of RC and AB inspiratory and expiratory differences are determined, and all differences more than +/−1 SD (third outliers) from the mean are discarded resulting in final sets of RC and AB inspiratory and expiratory differences. These final sets are then used to determine K according to the above formula.

More generally, this improved method includes methods with fewer or more steps of outlier elimination and methods with different elimination criteria (elimination criteria being increasingly stringent in later steps compared to earlier steps). For example, a two step method is applicable to more stable data employs elimination criteria of approximately +/−2.5 SDs and +/−1.5 SDs. Another embodiment applicable to less stable data has four elimination steps employing the successive criteria +/−4 SDs, +/−3 SDs, +/−2 SDs, and finally +/−1 SD.

A further calibration improvement employs a plurality of sets of calibrations coefficients (K and optionally M), each set appropriate for a particular behavioral state of the subject and used when the subject assumes that behavioral state. This is advantageous because the calibration coefficient(s) observed to be dependent on the state of the monitored subject. In particular, K is affected by subject posture, for example, supine, reclining, sitting, and standing, and by the intensity of subject activity (as it affects respiratory rate). In one embodiment of this improvement, RC and AB signals suitable for calibration are measured from time-to-time. The subject may be instructed to periodically perform the calibration process, for example, every half hour, every hour, or so forth, so that recorded RP data has calibration information necessary for re-determining the calibration coefficient(s). Also, the subject may be instructed to perform the calibration process when a significant change in behavioral state is signaled, perhaps by means of an entry in the data recording unit (3 in FIG. 1) or perhaps from processing of accelerometer data.

In a further embodiment, breathing calibration is performed at the commencement of subject monitoring in several behavioral states expected during the subsequent monitoring period. For example, breathing calibration data may be obtained with the subject supine, sitting, standing at rest, steady walking, and so forth. Calibration coefficient(s) are calculated from this data and are indexed by the subject state. Later during monitoring, a current behavioral state is determined from accelerometers (or other motion detector) signals, and the digitized and filtered RC and AB RP sensor data is combined to a Vt (and/or a Vol) signal using the pre-determined coefficients that correspond to the current behavioral state. Behavioral state—posture and activity—may be determined from filtered accelerometer signals as previously described.

A still further embodiment employs optimal linear estimation technology, in particular Kalman filter technology. Here, multiple sets of calibration coefficient(s) (K and optionally M) indexed by behavioral state form a linear respiratory model. The inputs to this model are RP signals, preferably RC and AB RIP sensor signals, and indicia of behavioral state as derived, for example, from concurrent accelerometer data. The calibrated output thereby response moment-by-moment to the current behavioral state of a monitored subject with an increased level of resolution. The output(s) of the model are a Vt (and/or Vol) signal, which may be compared with actual measurement or a currently determined Vt (or Vol) value. Accordingly, Kalman filter or predictor-corrector technologies may be routinely applied as known in the art to obtain optimal estimates of relative or actual current lung volumes. See, e.g., Maybeck, 1979, *Stochastic models, estimation, and control*, Academic Press, New York. Further, with a calibration signal, adaptive technologies may be applied in a routine manner to improve or refine previously determined model coefficients. See, e.g., Widrow et al., 1985, *Adaptive Signal Processing*, Pearson Education, Singapore, especially chapter 9 (Adaptive Modeling and System Identification).

5.2.5 Artifact Recognition And Baseline Determination

Next, the Vt signal, preferably but not necessarily derived from the previous processing of RP or RIP signals, and optionally a Vol signal, are further processed (31 in FIG. 2) to determine respiratory parameters, to recognize and eliminate artifacts (remaining after the prior filtering), and to establish baseline values for respiratory parameters that are useful for recognizing respiratory events (e.g., coughs, sighs, etc.) (35 in FIG. 2). The Vt signal is proportional to lung volume and may be in arbitrary units; the Vol signal reflects actual lung volume changes and may be in liters. Also available for further processing are the original digitized and filtered RP sensor signals. FIG. 4A illustrates (time increasing to the right) an exemplary Vt signal with four normal breaths. Also illustrated is its time derivative signal, dV/dt (labeled in FIG. 4A as dVt), which can be calculated by known methods of numerical differentiation. Since Vt is proportional to lung volume, dV/dt is proportional to respiratory airflow.

Various respiratory parameters may be derived from these signals, for example, for breath 74 in the Vt signal and for breath 76 in the dV/dt signal. For example, breath 74's inspiratory volume 78 is the difference between the maximum of this breath's Vt (end inspiratory volume) and the immediately preceding Vt minimum (previous end expiratory volume); and this breath's expiratory volume 80 is the difference between this breath's Vt maximum (end inspiratory volume) and its immediately following Vt minimum (current end expiratory volume). This breath's peak inspiratory flow (PIF) 82 is the maximum of the dV/dt; and its peak expiratory flow (PEF) 84 is the dV/dt minimum. A further respiratory parameter (not illustrated) is the inspiratory/expiratory ratio (IE ratio), which is the ratio of a breath's inspiratory time to its expiratory time, where the inspiratory time is the time between a breath's Vt maximum (end inspiratory volume) and its immediately preceding Vt minimum (previous end expiratory volume), and where the expiratory is the time between a breath's Vt maximum (end inspiratory volume) and its immediately following Vt minimum (current end expiratory volume). Additional respiratory parameters can be routinely derived from these parameters and the input signals.

Respiratory parameters determined for successive breaths form a time-ordered sequence of values. These time sequences of respiratory parameters along with the Vt (and/ or Vol) signal and optionally the primary sensor data, is then available for further processing, in particular for artifact removal, baseline determination, and respiratory event recognition (35 in FIG. 2).

A. Artifact Removal

It is preferred to further recognize and often discard artifact breaths and the parameter derived therefrom. Such artifact recognition is preferably performed by applying one or more rules that represent the evaluations made by one skilled in respiratory signal interpretation and physiology. Generally, these rules may be applied by known paradigms of rule-based processing according to which a rule engine applies encoded rules. Thereby, further rules may be added or particular rule sets chosen for particular application. The following rules have been found to be broadly useful, A first "outlier elimination" rule discards breaths with extreme parameters. FIG. 3C is an exemplary histogram of the amplitudes of the values of a particular respiratory parameter, having on the horizontal axis the parameter amplitude and on the vertical axis the relative number of parameter values with the corresponding parameter amplitude found in a measured sequence. Normally, such a histogram reveals a broad range of amplitudes between a number of small amplitude events and a tail of large amplitude events. The small amplitude events to the left of amplitude threshold 70 are usually due to remaining noise, cardiac, and other non-respiratory components. Large amplitude events to the right of amplitude threshold 72 are usually due to remaining motion and similar artifacts. Thus the first rule discards breaths with parameter values less than a low-amplitude threshold or larger than a large amplitude threshold. In order not to discard valid respiratory events such as sighs, coughs, and the like, these thresholds are usually set no lower than about +/−3 SDs from the mean or mode of the amplitude histogram.

Further rules are known herein as the "less than 25% rule" and the "true breath rule". The "less than 25% rule" marks breaths with inspiratory or expiratory or both volumes less than a pre-determined threshold value. Marked breaths are not considered in further processing and parameter values deriving from these periods are preferably discarded. Preferably, the pre-determined threshold is taken as an initial Vt calibration times a pre-determined ratio. The initial Vt calibration (Vt-cal) is preferably the mean of the inspiratory or expiratory or both volumes measured during the calibration period (or during a five minute window during the initial calibration period). Thus the volumes used to find Vt-cal are those that have survived the single step or multi-step elimination of outliers. A generally preferably pre-determined ratio (r1) has been found to lie between 20% and 30% and more preferably between 24% and 26% with 25% used in the following. However, this ratio may be individualized for each subject by using subject measurements and assessments to best recognize low-amplitude artifacts.

The "true breath rule" marks breaths as more likely to be "true" breaths than artifacts if the difference of the previous end expiratory volume (immediately preceding Vt minimum) and the current end expiratory volume (immediately following Vt minimum) is less than a fixed ratio times Vt-cal. A generally preferred fixed ratio (r2) has been found to lie between 200% and 300% and more preferably between 240% and 260% with 250% used in the following. Again, this ratio may be individualized for each subject by using subject measurements and assessments to best recognize low-amplitude artifacts.

B. Baseline Determination

Next baseline values of the respiratory signals and parameter sequences are determined for subsequent use in assessing deviations in respiratory performance. Baseline values are preferably determined by a moving median filter, which is known to return the statistical median of a group of observations. As applied, the median filtered value at the current time of a respiratory parameter is the statistical median of the set of (valid, non-artifact) values of this parameter that occur in a time window that includes the current time.

The window is chosen as a compromise between responsiveness to change (smaller window size) and insensitivity to noise and artifact (larger window size). Because each parameter may have different rates of change, noise characteristics, artifact sensitivity, and so forth, it is advantageous to select window characteristics separately for each parameter. Generally, preferred window sizes vary from 1 to 1.5 to 3 and up to 5 min., with 1-2 min being usually suitable. Also depending on the parameter, the window position may be leading, centered or lagging about the time of the current time. For example, 1 min. centered windows have been found generally useful for breath volumes, while 0,5 min (about 9 breaths) windows (approximately 0.5 sec) have been found generally useful for breath times (for example, inspiratory time). Also, it may be advantageous to individualize window characteristics for particular subjects whose recorded signals may have varying characteristics.

5.3 Event Recognition

Respiratory events are recognized (35 in FIG. 2) from the time courses of the respiratory signals and sequences of respiratory parameters that have been previously determined. This invention includes automatic event recognition 35, often by more than one method, of apneas 37, hypopneas, 39, sighs 41, coughs 43, and speech 45. Additional events may be similarly recognized from the signals and parameter sequences. Manual review of signals and processed clinical data by a responsible care giver is often required for proper patient card.

5.3.1 Apnea Recognition

A period of nearly absent respirations is recognized as an apnea if one or more of the breath volume parameters—inspiratory, expiratory, or tidal volumes—are less than a pre-determined threshold times that breath parameter's running median baseline, which is preferably determined using a window of one (1) to five (5) minutes leading the current breath. Preferably, the pre-determined threshold is between 1 and 50% and more preferably between 15 and 30%. Further, the period of reduced respiration should last for a pre-determined duration of between 5 and 60 secs. and more preferably between 8 and 20 secs. For many subjects, a two minute window, a threshold of 25%, and a period of 10 secs. result in adequate apnea recognition; these values may be individualized to particular subjects in view of past monitoring data.

Since respiratory events with breath volume parameters of 25% or less of baseline may have been discarded by previous artifact-removal steps, apnea may alternatively be recognized if the total time between two true breaths (see preceding section) is between more than 5 secs. and more than 60 secs.; more preferably the total time is more than 8 secs., and still more preferably, more than 10 secs. Apneic periods are preferably excluded from the running medians of the respiratory parameters.

FIG. 5B illustrates an exemplary apneic period observed from an actual sleeping subject. It can be readily seen that between times 110 and 112 breath volumes were substantially less than 25% of the preceding baseline. The duration between time 110 and 112 is approximately 19 secs.

A. Apnea Classification

Apneas may be generally classified as obstructive apneas (due to airway obstruction), central apneas (due to decreased CNS respiratory drive), or mixed apneas (with elements of obstruction and decreased drive). Apneas recognized according to the criteria above may be classified as to cause using additional parameters: respiratory phase relation (known as "ePhRL" or "phase relation") and of respiratory effort rate ("effort").

The phase relation is determined breath-by-breath by reference to the digitized, filtered RC and AB signals. RC and AB are considered to be in phase (or coordinated) if both signals reflect movements in the same direction, both either increasing during inspiration or decreasing during expiration. These signals are considered out of phase (or uncoordinated) if they reflect movements in opposite directions. A preferred numerical measure, ePhRL, of this phase relation is the percentage of time during a breath that the RC and AB signals are out of phase. ePhRL less than approximately 40% signifies normal breathing to mild respiratory un-coordination, while a value greater than 40% approximately signifies moderate to severe respiratory un-coordination. Accordingly, obstructive apneas are characterized by a percentage close to one and central apneas by a percentage close to normal. A preferred threshold for separating low and high percentages is between 20% and 60% with 40% is generally suitable; the threshold may be individualized to particular subjects.

FIG. 5B also illustrates these respiratory phase relations. Outside of the illustrated apneic period, before time 110 and after time 112, observation of this figure reveals that the RC and AB signals are in phase, both moving together in inspiration and expiration, with ePhRL in a normal range. During the apneic period, between times 110 and 112, these signals are out of phase, the RC attempting to inspire while the AB is attempting to expire, and vice versa, with ePhRL close to 1.0 signifying an obstructive process.

Effort rate is the rate of breath efforts, where a breath effort is recognized by breath volume parameters between 1% and 25% of the running median for that volume parameter. Preferably, a breath effort is recognized by a tidal volume between 5% and 25% of the running median tidal volume, the median preferably being from a leading two minute window. The baseline for the breath effort rate is the median breath rate, the median preferably being from a leading window of 10 breaths.

In terms of these additional parameters, it is preferred to classify an apneic period as obstructive if the ePhRL is greater than approximately 40% and if the breath effort rate is greater than approximately 75% of baseline breath. An apneic period is classified as central if either ePhRL is less than approximately 40% or if the breath effort rate is less than approximately 0-25% of baseline.

5.3.2 Hypopnea Recognition

A period of reduce respirations may be recognized as an hypopnea according to the breath parameters used in apnea recognition but with relaxed thresholds. Preferably, hypopnea, or reduced respiration, is recognized by comparison to a running median baseline from a window with a one (1) to five (5) minute duration leading the current breath. Preferably, the pre-determined threshold is between 20 and 80% and more preferably between 25 and 50% of the running median baseline. As in apnea recognition, the period of reduced respiration should last for a pre-determined duration of between 5 and 60 secs. and more preferably between 8 and 20 secs. For many subjects, a two minute window, a breath-volume threshold of less than 50% and greater than 25%, and a period of 10 secs. result in adequate hypopnea recognition; these values may be individualized to particular subjects in view of past monitoring data.

Hypopneic periods are classified as obstructive, central, or mixed in a manner to the similar classification of apneas. Hypopneic periods are preferably included in the running medians of the respiratory parameters.

5.3.3 Sigh Recognition

The present invention also recognizes sighs. A higher than usual frequency of sighs often signifies psychological distress, such as anxiety reactions or depression. Anxiety is often increased during periods of breathing difficulty occurring in the course of lung diseases.

First, to exclude motion artifacts, signs are true breaths (defined in the preceding section) with expiratory periods preferably greater than a pre-determined threshold having a range of from 0.25 to 3 secs. A preferred threshold is approximately 1 sec, which may be individualized. Breaths meeting these requirements are recognized as sighs if their inspiratory or expiratory or tidal volumes are greater than a predetermined threshold time the running median baseline value (preferably, determined from a leading, two minute window). The preferred threshold, for example, of Vt, is between 100 and 1000%, while for many subjects a threshold of approximately 250% results in adequate sign recognition. This threshold may be individualized to particular subjects in view of past monitoring data.

FIG. 4B illustrates sigh 90 in data recorded from an actual subject. Here, Vt 90 is approximately 600% of the running median Vt baseline. This sigh is also represented in the air flow signal, dV/dt, as a readily visible peak 92 which proportionately reflects and confirms the increased breath volumes.

5.4 Speech Recognition

Recognition of whether or not a monitored subject is speaking is important because speech often defines a context which qualifies the meaning of respiratory, cardiac, and other physiological signals. The quantity and quality of physiological activation during speech is known to depend on cognitive, emotional, and often related physical factors, such as loudness and rapidity. These may vary according to the social and interpersonal qualities of the interaction that gives rise to speech and to emotions elicited. Thus, physiological effects of speech are likely to be different in private vs. public settings, in boring conversations vs. engaging ones, and in light conversation vs. argumentative debates. Personality, social anxiety, shyness, and the like may influence these reactions but are currently unexplored in ambulatory settings. Most social interactions in daily life involve speech and by monitoring the occurrence of speech, social interaction can be quantified. Certain disorders may be characterized by an increase (e.g., mania) or reduction (e.g., depression) in social behavior. Social isolation is frequently observed in the elderly and has been shown to be related to unfavorable changes in autonomic nervous system functioning.

Because speech is a more complex and potentially individual performance that may correspondingly affect respiration, this section presents first a general method by which appropriate parameters and thresholds for speech recognition may be determined, and subsequently, an application to groups of healthy subjects.

5.4.1 Parameter and Threshold Determination

This invention also provides systematic methods for selecting parameters and their thresholds for recognizing speech in individual subjects and in groups of similar subjects. Although described with respect to speech in the following, these methods may also be applied to select alternative parameters for recognizing other respiratory events, such as the coughs, sighs, and so forth. Generally, these methods involve measurements in various speech and non-speech conditions and then processing the measured data to determine the parameters and thresholds most suited to recognition of speech (or of other respiratory events).

Accordingly in a first step, the intended subject or representatives of the intended group of subjects are instructed to engage in speech activities and also in non-speech activities. The non-speech activities may include sitting, resting, walking, light activity, and so forth. The speech activities may or may not be accompanied by these non-speech activities. Further speech activities may occur in various social settings, for example, reading aloud or a multi-person conversation. Ambulatory RIP recordings of respiratory signals and parameters are made (preferably as described above) during these various types of activity, and the measurements are segregated and separated by activity.

A variety of pattern recognition and classification techniques may be applied to the grouped data to discern patterns of parameters and values capable of distinguishing the data groups with suitable accuracy. Suitable accuracy for recognizing speech in order to provide a physiological context may be a false negative or positive rate of between 20% and 10% or better. Other applications may require other level of accuracy. Pattern classification techniques may include statistical approaches, such as regression, discriminant, and analysis of variance technologies, or automatic grouping or ordering by, for example, k-means clustering or neural networks. See, for example, Duda et al, 2000 $2^{nd}$ ed., *Pattern Classification*, Wiley Interscience, New York. Preferred outputs are single parameters or functions of several parameters along with threshold values that may be used for recognition of speech or non-speech, and optionally for recognition of speech types.

5.4.2 Speech Recognition

This method has been to recognizing speech versus non-speech periods in RIP recordings from ambulatory subjects. Generally, from linear discriminant analysis, several single parameters and linear combinations of 2-4 parameters have been identified that provide false negative or positive recognition accuracy at the 1-15% level. These parameters and combinations do not require significant computation, and can be routinely applied to ambulatory recordings of from several hours to one-half of more of a day.

Preferred recognition parameters include inspiratory/expiratory (IE) ratio, fractional inspiratory time, inspiratory flow rate, and expiratory time, and linear combinations and percentage coefficient of variation thereof. These parameters all performed well in detecting speech, but the IE-ratio—the ratio of inspiratory time to expiratory time (with a threshold of approximately 0.52)—is more consistently and is most preferred. This single parameter has advantages including: 1) it is easy to measure since it does not require volume calibration like, e.g., inspiratory flow rate, and 2) it can be determined for each individual breath, while variability parameters require at least 1-min measurement periods. Such speech recognition is further described in Section 6.

Although the IE-ratio with a fixed cutoff of 0.52 is most preferred for healthy individuals, certain other populations, e.g., patients with chronic obstructive pulmonary disease or asthma, may require different IE-ratio cutoffs or even different parameters or combinations. Further, speech recognition parameters can be individualized for other populations and even individuals using the same methods, e.g., linear statistical analysis.

5.5 Dyspnea and $FEV_1$ Monitoring

The present invention provides methods for continuously monitoring indicia of and surrogates for patient dyspnea and $FEV_1/VC$, both of which clinically important.

A. Monitoring Dyspnea

Dyspnea is a sensation of difficult or labored breathing, a feeling of breathlessness, or an experience that breathing efforts are not fully satisfied, and is considered by many to be a direct or indirect consequence of pulmonary hyperinflation. Hyperinflation disorders the normal relationship between ventilatory effort and actual air intake, or the perception of air intake, and a patient's attempts to breathe do not move the intended amount of air. For example, hyperinflation alters the resting lengths of the diaphragm and intercostal muscles outside of their optimal ranges, decreasing force generated and thereby, also, decreasing airflow for a given neural respiratory drive.

Dyspnea is common in patients with asthma or with chronic obstructive pulmonary disease (COPD), e.g., pulmonary emphysema and chronic bronchitis, and is an important symptom in the assessment and management of these and other diseases. Asthma can lead to hyperinflation because associated broncho-constriction greatly increases airway resistance; can COPD can also do so because associated increased lung compliance decreases lung recoil thus limiting airflow. As these conditions worsen, airflow does not normally respond to increased respiratory drive leading to anxiety and occasionally to panic.

Dyspnea, being a subjective assessment, is currently assessed patient questioning. But patients may tire of repeated questioning and even become habituated to the sensation of breathlessness. Consequently, objective measures of ventilatory drive shown to be linked to sensations of dyspnea would be clinically valuable. At a given activity level, such ventilatory drive measures should remain relatively constant, and thus increases in ventilatory drive would then indicate patient difficulty.

The present invention provides such objective indicia of ventilatory effort related to dyspnea that, importantly, depends on respiratory parameters readily determinable from the previously described Vt and/or Vol signals. A preferred dyspnea indicia is the ratio of minute ventilation volume ($V_E$) to peak inspiratory flow rate ($P_IF$), that is the ratio $V_E/P_IF$. This ratio decreases as end expiratory lung volume (EELV) increases, that is with progressive hyperinflation, and as discussed, is therefore associated with dyspnea. FIG. 6 evidences the dependence of $V_E/P_IF$ on pulmonary hyper-inflation. Here, hyperinflation was induced by placing a subject on 10 cm $H_2O$ of positive end expiratory pressure (PEEP). After PEEP commences, EELV dramatically increases by about 3 liters as the subject's lungs are expanded with the positive end-expiratory pressure; and, after PEEP terminates, EELV begins to return to normal. The mechanical changes associated with increased EELV (hyperinflation) impair airflow leading to decreasing $V_E$. The subject then attempts to compensate by increasing respiratory neural drive to the diaphragm and the intercostal muscles, leading to increased $P_IF$ (airflow). Therefore, the $V_E/P_IF$ ratio decreases, here by at least a factor of 3. Thus hyperinflation, which is associated with dyspnea, leads to decreased $V_E/P_IF$.

In summary, $V_E/P_IF$ serves as an index of respiratory muscular efficiency and breathlessness. It links drive from the respiratory center as measured by Pif/Vt to the output of the respiratory system as measured by ventilation. In patients who have inefficient respiratory muscular contractions because of dynamic pulmonary hyperinflation, respiratory drive is increased to a disproportional extent relative to any changes in ventilation so that this ratio falls.

A subject's $V_E/P_IF$ ratio can be easily monitored by the systems and methods of this invention on a continuous, or on a quasi-continuous, or on an intermittent, or on an as needed basis such as during episodes dyspnea, and diagnostic thresholds defined. $V_E$ can be easily determined as the sum of the inspiratory or expiratory volumes (78 and 80 in FIG. 4A) occurring in time period such as a minute, or by the product of an average inspiratory or expiratory volume with respiration rate. $P_IF$ (82 in FIG. 4A) can be determined as the derivative of the respiratory volume curve. The value of the $V_E/P_IF$ ratio should be substantially independent of whether these parameters are measured from the Vt curve, which is proportional to lung volume, or from the Vol curve which reflects changes in actual lung volume. Further, $V_E/P_IF$ ratio threshold can be determined, either for a population or for an individual. For example, a first threshold may be chosen at the usual onset of subjective dyspnea; a second threshold may be chosen at the onset of a possibly dangerous level of dyspnea.

B. Monitoring $FEV_1$

The forced expiratory volume in 1 second, known as $FEV_1$, is the accepted measure of airway adequacy and patency. This standard measurement is performed by having a subject expire with maximal effort as rapidly as possible starting from a maximal lung volume (after a maximal inspiration) and continuing all the way to residual volume. An important indicia of pulmonary disease and its progress is the ratio of $FEV_1$ to vital capacity (VC), that is $FEV_1/VC$. Typically, healthy subject have ratios of at least 80-85%, while subjects with asthma or COPD have $FEV_1/VC$ ratios of 70% or less, a value which drops as COPD worsens Or as an asthma attack begins and progresses.

Although $FEV_1/VC$ is widely used and relied on, measurement of this ratio on even an intermittent basis is fatiguing. $FEV_1$ is conceptually simple but requires maximal effort from a subject. Similarly, though simple, measurement of VC requires that a subject expire completely, which becomes especially demanding as lung volume nears residual volume. Thus, repeated $FEV_1/VC$ measurements are likely to be fatiguing and thus often inaccurate, especially in subjects with pulmonary problems in the first place. Therefore, surrogates for or indicia of $FEV_1/VC$ (or of its impending changes) easily measurable during normal respiration would be widely beneficial.

The methods and systems of the present invention provide continuous monitoring of ventilatory parameters that have been discovered in combination to be a sensitive and less intrusive measure of present or impending airway disturbances. These combinations generally can be used as surrogates for or indicia of the $FEV_1/VC$ ratio. One such combination is the ratio of peak inspiratory flow, $P_IF$, to tidal volume, $V_T$. This ratio, namely $P_IF/V_T$, has been discovered to be sensitive to changes in flow-rate in a manner reflecting the $FEV_1/VC$. A further combination is the time to reach peak expiratory divided by the expiratory time. The time to reach peak expiratory is the time from the start of expiration (a maximum of the Vt signal) to the minimum of the dVt/dt (the maximum outward airflow); the expiratory time is the total time from the start to the end of expiration. An additional combination of variables that track changes in $FEV_{1.0}$ of greater than 20% as evaluated by multiple linear regression (sensitivity and specificity are equal to 0.90; ROC analysis revealed an area under the curve (AUC) of 0.89) are the ratio of peak to mean expiratory tidal flow ($P_EF/M_EF$), the rib cage contribution to the tidal volume (% RC), and the fraction of expiratory time with thoraco-abdominal asynchrony. These parameters may be continuously or intermittently monitored by the systems and methods of this invention as previously described to allow breath-by-breath analysis of $P_IF/V_T$, $P_EF/M_EF$, % RC and fraction of expiratory time with thoraco-abdominal asynchrony.

These parameters and indicia are readily determined from examination of processing of the Vt (and/or Vol) signals previously described. Thus these indicia enable airway disturbances to be monitored in a manner independent of patient effort and the potential confounding factors associated with inadequate patient effort. Consequently, this effort independent assessment of airway patency can provide early warning to indicate the onset or early stages of airway changes in acute disease and in crises during chronic disease.

5.6 Methods of Cough Detection

The present includes alternative embodiments of cough detection and classification methods (43 in FIG. 2). Cough detection is important because, for example, an increasing cough frequency is also an early sign of acute pulmonary edema which often accompanies cardiac failure. Generally, these methods proceed by recognizing candidate respiratory events from input respiratory parameters including AB, RC, and $V_T$ signals and, optionally, candidate sound events from audio input. Then coughs events are detected from particular combinations of candidate respiratory events and associated candidate sound events. Types and severity of coughs may be discriminated by the values of the respiratory and sound event parameters.

5.6.1 A First Method for Cough Recognition

According to a first cough detection method, coughs must be recognized as true breaths preferably with expiratory periods greater than a pre-determined threshold having a range of from 0.25 to 3 secs. A useful and preferred threshold is approximately 1 sec, which may be individualized. Then, breaths meeting these criteria are recognized as coughs if their peak expiratory flow (PEF) is greater than a pre-determined threshold of the running median baseline PEF value as determined from a leading, two minute window. The preferred PEF threshold is between 100 and 1000% or greater of the running median baseline PEF value. For many subjects, a PEF threshold greater than approximately 250% results in adequate cough recognition; this value may be individualized to particular subjects in view of past monitoring data.

FIG. 4C illustrates two coughs 94 and 98 in data recorded from an actual subject. PEF is determined from the dV/dt curve in which the same two coughs 96 and 102 are readily visible as short sharp exhalations. Here, PEF for cough 96 is approximately 400% of the running median PEF baseline, while for cough 102, the PEF is approximately 380% of the baseline.

5.6.2 An Alternative Method for Cough Recognition

FIG. 7 illustrates an alternative method for cough detection which specifically incorporates sound input as an aid to cough detection. In this figure and subsequently in this subsection, input data and derived data are often referred to by the following abbreviations:

RC Ribcage (RC) measurements (input data)
AB Abdominal (AB) measurements (input data)
HFB High frequency band pass filtered Vt (derived data)
LFB Low frequency band pass filtered Vt (derived data)
FAB High frequency band pass filtered AB (derived data)
$V_T$ Tidal Volume (method input data derived as described from the RC and AB measurements)
MIC Microphone audio signal recorded from a throat microphone (input data)
SE Microphone audio signal envelope (derived data)
PITCH Audio pitch level (derived data)
PITCHm Mean audio pitch level over finite time duration (derived data)
EVT Audio event and duration detector (method step)
CGH Cough marker (method output data indicating presence of a detected cough)

In summary, FIG. 7 illustrates that the Vt and AB signals first are band pass filtered by two band pass filters designed to further limit (if not already sufficiently limited) high frequency noise and low frequency movement artifacts. If the filtered signals have peak-to-peak power (or breath amplitudes, which is the difference between maximum expiration and maximum inspiration) exceeding a predefined threshold, −T, then both respiratory and audio signals are examined in more detail to detect the presence of a cough event.

Audio signals (from, for example, a throat microphone) are processed with a speech recognition front-end to determine if an audio event contains voiced or unvoiced speech. Important to this determination is the derived signal PITCHm, which is the mean of pitch values over a finite duration. This mean level should increase significantly if the subject is speaking or engaged in a conversation, and not increase in the case of a cough. The pitch value is computed by measuring the peak-to-peak power present in the Cepsturm or Mel Frequency Cepstral Coefficients (MFCCs). Another important derived signal is the PITCH signal. Output from audio signal processing are pulses, as illustrated by the EVT trace in FIG. 9, with timing and duration equal to that of significant audio events detected in the input sound data.

In the absence of a sound event, no cough is detected. If a sound event is present, its duration determines which filtered respiratory signals should be applied to the cough signature detector. If the duration of the sound event is relatively long (that is longer than the median significant sound event), e.g., >=600 msec, the low frequency band pass filtered respiratory data, LFB, is analyzed by the cough detector. If the audio duration is relatively short (that is longer than the median signification sound event), e.g. <=600 msec., the high frequency band pass respiratory data, HFB, is analyzed. This signal selection has been found to lead to adequate filtering of movement and motion artifact so that cough signatures may be more clearly detected. Various cough signatures are illustrated subsequently in FIGS. 9, 12A-B, 13A-B, and 14A-B.

5.6.3 Step Details—Digital Filters and Peak Power Determination

The tidal volume trace Vt, which is the linearly weighted sum of the RC and AB bands, is passed through 2 FIR band pass filters in parallel and the peak power (as reflected by the maximum of the filtered signal) is measured to determine the existence of a possible event (if the peak power exceeds a threshold T). Filters for the input respiratory signals are preferably of the finite impulse response (FIR) design, although infinite impulse response (IIR) filters with a minimal phase shift or time delay may be used. Here, respiratory signal phase must be sufficiently unperturbed so that it remains temporally coincident with the corresponding audio signals.

A filter length of 1024 was determined as the preferably length to achieve sufficiently sharp characteristics. FIGS. 8A-B illustrate the frequency and phase responses of the low and high band pass filters described above. Table 2.1 lists the parameters of these preferred respective filters.

TABLE 2.1

Mat lab FIR filter design parameters.

| Signal | Stop 1 Freq (Hz) | Pass 1 Freq (Hz) | Stop 2 Freq (Hz) | Pass 2 Freq (Hz) | Stop 1 Attenuation (dB) | Pass Attenuation (dB) | Stop 2 Attenuation (dB) |
|---|---|---|---|---|---|---|---|
| LFB | 0.4 | 0.5 | 4.9 | 5.0 | 80 | 0.5 | 80 |
| HFB | 1.0 | 1.1 | 4.9 | 5.0 | 80 | 0.5 | 80 |

These filters were designed using Matlab™ FIR least-squares method with model order 1024. The parameters for the filters described above are chosen to filter to the extent possible subject physical movement while retaining sufficient respiratory movement captured from the rib cage and abdomen (RC and AB).

A. Power Threshold

The peak-to-peak power, which is preferably defined herein measured as the maximum point on a positive going signal to the minimum point on a negative going signal, is used to determine if a candidate cough event is present in the filtered respiratory signal. If this threshold is not passed, no significant cough is considered to be present. Signals LFB, HFB, and FAB are measured to make this determination. Signal FAB is the filter residual from the AB filtered trace, and is advantageous in the event that RC and AB are out of phase and a have a subtraction effect on Vt decreasing the true effort in the bands. The threshold –T is loosely generally approximately 200 ml expired volume, although it can be adjusted for particular populations of specific individuals.

5.6.4 Step Details—Audio Event Detector

FIG. 9 illustrates an exemplary sound envelope-trace SE—derived from an exemplary microphone input-trace MIC. The sound envelope is preferably down sampled to the same sample frequency as all respiratory bands, that is preferably 50 Hz. This minimizes the effects of filter residuals and derivations of the respiratory signals. This down sampling involves averaging every 30 samples from the microphone stream, which is sampled at 1500 Hz yielding a 50 Hz sound envelope.

Next, the sound envelope signal is processed for audio event detection and duration determination. The start of an audio event is recognized when the sound envelope passes a threshold determined to be a multiple of the calibrated background noise threshold. Preferably, the noise threshold is calibrated from long term microphone recordings (up to 240 hours has been used) and is determined by monitoring a signal variation of between +1 and −1, which represents a level of 30 on the sound envelope signal. An advantageous event threshold has been found to be twice the noise threshold, or a value of 60. The audio event ends when sound envelope drops back below the noise threshold (here, a value of 30). Use of a throat microphone minimizes the influence of background noise. An audio event is marked in the EVT trace as a pulse of amplitude 10 and duration equal to the length of the audio event. FIG. 9 illustrates an audio event and also an accompanying HFB signal.

5.6.5 Step Details—Cough Signature Detector

If a significant audio event coincides with a possible respiratory event, one of these signals is selected depending on the audio duration and further analysed for a cough signature. Having determined the duration of a significant audio cough event either the LFB signal or HFB signal is further analyzed for the presence of a cough signature. To aid selecting the pass band to analyze, the audio event cough duration is measured. For short audio event durations, that is for cough events less than about 600 ms, the HFB is analyzed as shorter cough events are likely to have higher frequency components (in order to expire a cough in shorter time). Conversely, coughs of longer time duration result in lower frequency signals so that the LFB signal is chosen for the cough signature detection.

A typical cough signature is shown in the HFB trace of FIG. 9. A cough signature preferably has a sharp expiration (corresponding to a high peak expiratory flow) followed by a sharp inspiration in either the HFB or LFB traces or both, that occur in association with an audio event classified as a cough event. The lowest sample value the HFB or LFB traces is preferably located close to the center region of the associated audio event. The center region is defined as those times that are greater than 33% of the audio event duration from the start of the audio event and less than 33% of the event duration from the event end. Furthermore, this minimum value must exceed the −T value and have a constant incline on either side of the center sample for the duration of the event. The −T value in this case may be calibrated based on the mean breath volume for the particular subject calculated during regions of identified quite or relaxed breathing. The difference between each sample [x(n)−x(n−1)] should therefore be negative before the center of the signature and positive after the center and before the end. Noise has been filtered from the signal and will not affect the calculation.

Moreover, the slopes of the HFB or LFB traces (and the gradients of these slopes) on either side of the minimum is preferably within the following constraints. First, the signature should be reasonably symmetrical with similar slopes on each side of the center sample of minimum. The end points of each slope on either side of the center sample or minimum. are the points where the signal reaches maximum amplitude before starting to decrease. These end points should not exceed a time duration greater than 50% of the event time duration past the end of the event or before the end of the event. By applying these tight constraints, the possibly of falsely detecting a cough like event are greatly reduced. Alternatively, thresholds may be specified that must be exceeded by the peak expiratory flow and the succeeding peak inspiratory flow.

5.6.6 Step Details—Frontend Processing

The step converts an audio waveform to a compact parametric representation (preferably a form of frequency versus time representation) so that cough sounds may be distinguished from speech sounds, the former generally having lower frequencies and the latter higher frequencies. Accordingly, a frequency-related threshold may be defined in the compact representation so that signals below the threshold are likely to be cough sounds.

A candidate event that has the respiratory signature of a cough is not considered to be a cough if the associated sound event is determined not to include cough sounds. Conversely, a candidate event that has the sound signature of a cough is not a considered to be a cough if the associated respiratory event does not have cough characteristics. An alternate test accepts a sound event as cough if the signal power below the cough-speech threshold increases even if there is signal power above the cough-speech threshold. A candidate event is also not considered a true cough if the PITCH value is above a certain threshold. Even if the PITCH value is just below this threshold, a candidate event will not be considered a cough if the PITCHm value is above this threshold, where PITCHm is the average of all PITCH values within a predefined time duration. If the average of these PITCH values is above this threshold, it is implied that there is speech before and after this event, and therefore this event is probably speech.

Figure 11A:
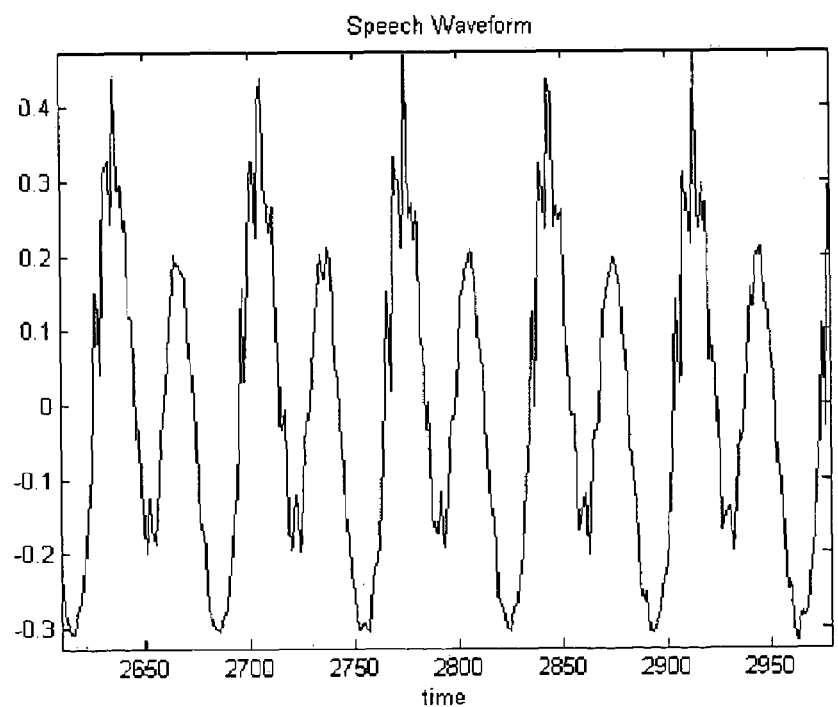

The characteristics of the speech audio signal are considered to be stationary over time increments of approximately 10 msec., and is therefore analyzed over such segments. An example of the stationary portion of a speech signal is shown in FIG. 11A. Over long durations, speech signal characteristics certainly change to reflect the different audio sounds being generated. Short-time spectral analysis is a known way to so characterize audio signals.

Several techniques are known for parametrically extracting and representing the pitch characteristics of an audio signal, such as Linear Prediction Coding (LPC), Mel-Frequency Cepsturm Coefficients (MFCC), and others. MFCCs have been found to be preferable in the cough detection methods. Generally, MFCCs are based on the known variation of the human ear's critical bandwidths so that these coefficients are express in the mel-frequency scale which is linear at frequencies less than 1000 Hz and logarithmic at frequencies above 1000 Hz. These filters capture the phonetically important characteristics of speech.

A. MFCC Determination

FIG. 10 is a flowchart of the preferred process of computing MFCCs. It process an audio input sampled at 1500 Hz, a sampling frequency chosen to resolve speech and cough components. The first step in this process, the frame blocking step, blocks the continuous speech signal into frames of N samples, with adjacent frames being separated by M samples (M<N). The first frame consists of the first N samples. The second frame begins M samples after the first frame, and overlaps it by N–M samples. Similarly, the third frame begins 2M samples after the first frame (or M samples after the second frame) and overlaps it by N–2M samples. This process continues until the entire audio has been blocked into one or more frames. Preferred blocking parameters N and M are N=64 (which is equivalent to ~40 msec. windowing and facilitates the fast radix-2 FFT) and M=32.

The windowing step windows each individual frame to minimize signal discontinuities at frames boundaries. Spectral distortion is minimized by using a continuous and smooth window to taper the signal to zero at the beginning and end of each frame. If a window is defined as w(n), $0 \leq n \leq N-1$, where N is the number of samples in each frame, then the result of windowing is the signal $$y_l(n) = x_l(n)w(n), \ 0 \leq n \leq N-1 \tag{4.1}$$

The Hamming window is preferably used in this invention. It is defined as:

$$w(n) = 0.54 - 0.46 \cos\left(\frac{2\pi n}{N-1}\right), \ 0 \leq n \leq N-1 \tag{4.2}$$

The next processing step is the Fast Fourier Transform, which converts each frame of N samples from the time domain into the frequency domain. The FFT is a well known algorithm for implementing the discrete Fourier transform (DFT), which is defined on the set of N samples $\{x_n\}$, as follow:

$$X_n = \sum_{k=0}^{N-1} x_k e^{-2\pi jkn/N}, \ n = 0, 1, 2, \ldots, N-1 \tag{4.4}$$

Figure 11B:
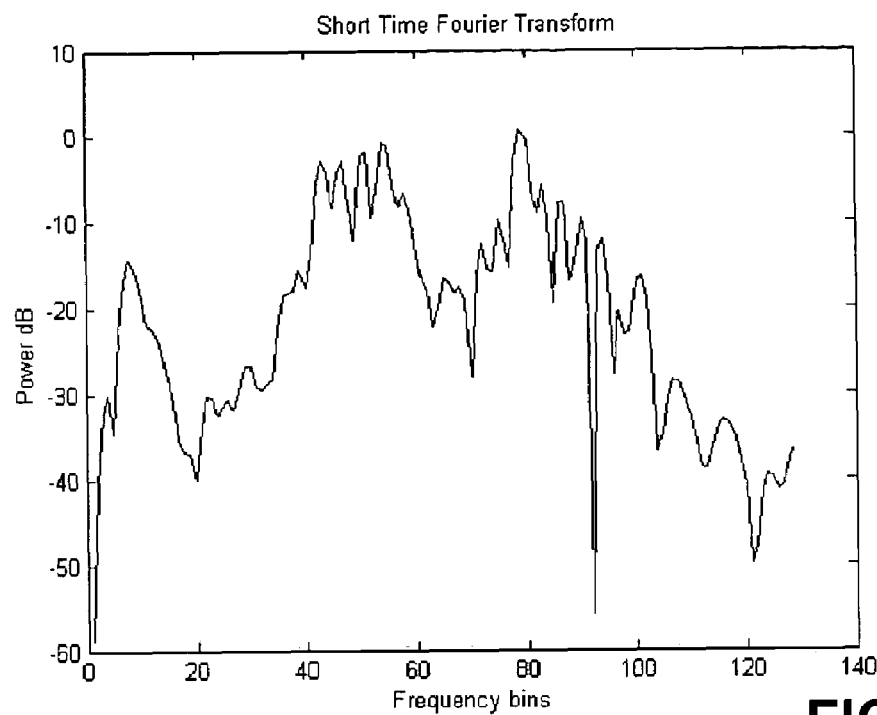

In general $X_n$'s are complex numbers. The resulting sequence $\{X_n\}$ is interpreted as follows: the zero frequency corresponds to n=0, positive frequencies $0 < f < F_s/2$ correspond to values $1 \leq n \leq N/2-1$, while negative frequencies $-F_s/2 < f < 0$ correspond to $N/2+1 \leq n \leq N-1$. Here, $F_s$ denotes the sampling frequency. The result of this step is often referred to as spectrum or periodogram. FIG. 11B illustrates the spectrum of the signal of FIG. 11A.

The next step is mel-frequency wrapping. Psychophysical studies have shown that human perception of the frequency contents of sounds for speech signals does not follow a linear scale. Thus for each tone with an actual frequency, f, measured in Hz, a subjective pitch is measured on a scale called the 'mel' scale, which has a linear frequency spacing below 1000 Hz and a logarithmic spacing above 1000 Hz. As a reference point, the pitch of a 1 kHz tone, 40 dB above the perceptual hearing threshold, is defined as 1000 mels. Therefore the following approximate formula computes mels. for a given frequency f in Hz:

$$\mathrm{mel}(f) = 2595 * \log_{10}(1 + f/700) \tag{4.5}$$

Figure 11C:
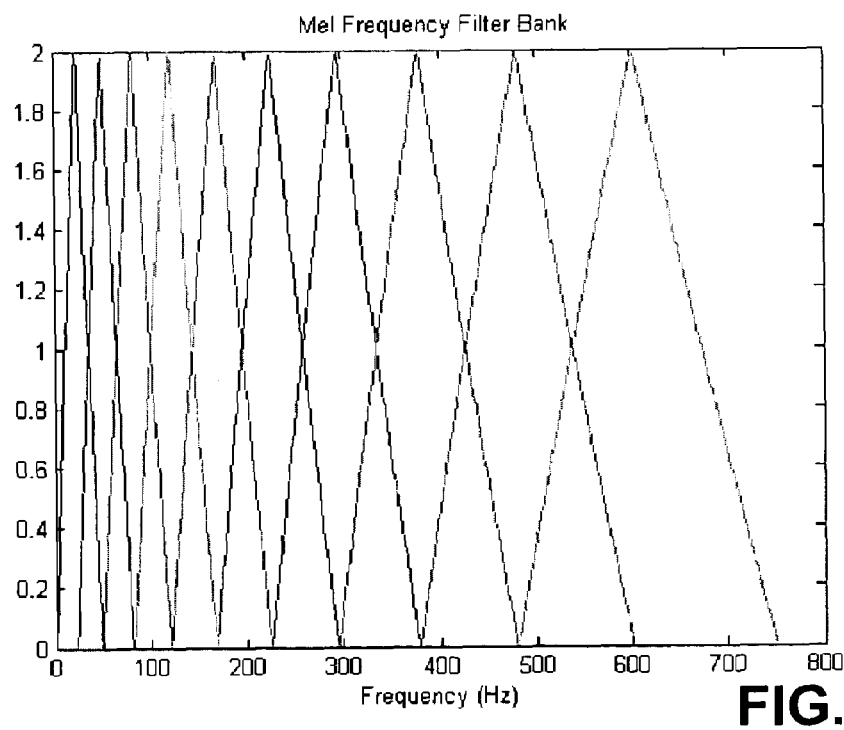

Simulating the subjective audio spectrum commonly is done by a filter bank, with filters spaced uniformly on the mel scale as illustrated in FIG. 11C. The filter bank has a triangular band pass frequency response, and the spacing as well as the bandwidth is determined by a constant mel frequency interval. The mel-filtered spectrum of an input signal, S(ω), thus consists of the output power of these filters when S(ω) is the input. The number of mel spectrum coefficients, K, is typically chosen as between 18 and 24. Note that this filter bank is applied in the frequency domain, therefore it simply amounts to multiplying those triangle-shape window coefficients of FIG. 11C with the time frequency spectrum of FIG. 11B. In this method, it has been found preferable to apply a K=10 mel scale filter banks to the input signal frequency spectrum due to the low sample rate.

In the final step of cepsturm determination, the log mel spectrum is transformed back to time resulting in the mel frequency cepstrum coefficients (MFCC). The cepstral representation of the speech spectrum provides a representation of the local spectral properties of the signal for the given frame analysis. Because the mel spectrum coefficients (and so their logarithm) are real numbers, they can be converted to the time domain using the Discrete Cosine Transform (DCT). Therefore if the mel power spectrum coefficients that are the result of the last step are denoted by $\tilde{S}_k$, k=1, 2, ..., K, the MFCC's, $\tilde{c}_n$, may be calculated as:

$$\tilde{c}_n = \sum_{k=1}^{K} (\log \tilde{S}_k) \cos\left[n\left(k - \frac{1}{2}\right)\frac{\pi}{K}\right], n = 1, 2, \ldots, K \quad (4.5)$$

Note the first component, $\tilde{c}_0$, is advantageously excluded from the DCT since it represents the mean value of the input signal that carries little speaker specific information.

Figure 11D:
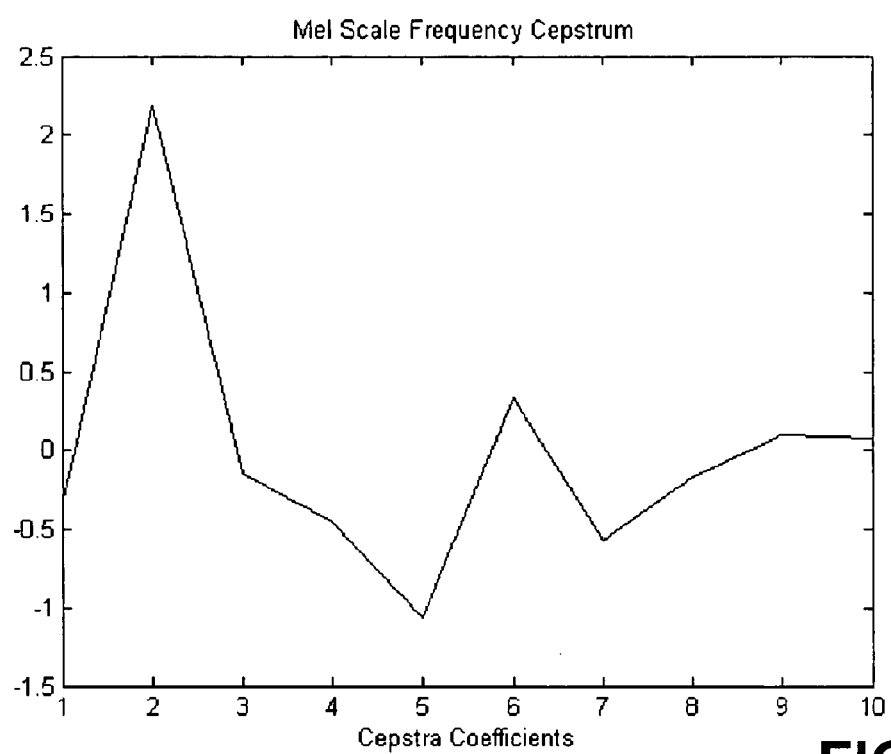

FIG. 11D illustrates the cepsturm output for the speech signal already presented in FIGS. 11A-C. Cough and unvoiced speech sounds have been found to generally fall below a me-frequency threshold of 1.5-2. It is evident that voiced speech is present in the exemplary signal because signal power is present above this threshold in the higher pitches. The PITCHm signal may be obtained as a simple mean, or a power-weighted mean, or the like of the mel-frequency spectrum. The PITCH signal is obtained as the maximum mel-frequency cepstral coefficient resultant from the discrete cosine transform.

5.6.7 Cough Examples

A. Chronic Obstructive Pulmonary Disease (COPD)

Chronic obstructive pulmonary disease (COPD) generally refers to a group of pulmonary disorders that lead to progressively worsening respiratory function. Two common causes of COPD that progressively impair airflow to the lungs are bronchitis and emphysema. In chronic bronchitis, the airways are blocked and inflamed, mucus producing glands in the bronchi are enlarged, and an excessive amount of mucus is secreted into the lungs. Therefore, this form of COPD leads to an increased need to cough in order to clear this excessive mucus.

FIGS. 12A-B illustrate COPD coughs that were identified by audio and video input to the systems and methods of this invention as implemented in a software application. The HFB and LFB traces illustrate that the true cough in FIG. 12A is characterized by sharp (short duration and high airflow) expiration followed by sharp inspiration. Further an audio event was detected from throat microphone input that was characterized as having a low pitch and most likely to include cough sounds. FIG. 12B illustrates several non-cough events and one true cough event from a COPD patient. The non-cough events are seen as low-pitched sound events that lacked accompanying respiratory cough indicia (sharp inspiration and expiration in the LFB or the HFB signals). On the other hand, the true cough event is characterized by associated sound and respiratory events having proper characteristics.

B. Cystic Fibrosis (CF)

Cystic Fibrosis (CF) is a life threatening multi-system condition that primarily affects the lungs and digestive system. CF leads to the secretion of sticky mucus obstructing the airways, and causing a need to cough frequently in order to try to clear the mucus from the airways. Coughing can loosen the mucus allowing easier breathing.

FIGS. 13A-B illustrate coughs from two CF patients. It is apparent from examination of the associated traces, especially the HFB and LFB traces, that these coughs are more severe than the COPD coughs, having greater amplitudes and/or higher airflows. Furthermore, the amplitudes are sufficient so that cough signatures are readily identified in the unfiltered tidal volume (Vt) trace.

C. Post-Infectious Cough (PIC)

Post-infectious cough (PIC) is most common after viral infections of the upper respiratory tract that induce coughing due to persisting inflammation regardless of any increased mucus secretion. FIGS. 14A-B illustrate two examples of PIC coughs.

5.6.8 Cough Severity and Classification

Detected cough events may be further analyzed by extracting particular characteristics of the band pass filtered lung volume data, the LFB and HFB signals. The characteristics include the depth or amplitude of the cough signature and the reflex inspiratory drive at the end of the cough signature. Measures that allow for a discrimination of the pathological causes of coughs include a ratio of the depth of cough with the mean expiratory volume calculated on a per subject bases during identified periods of quiet and relaxed breathing. This allows severity to be determined based in the individual calibration and therefore aids in determining lung disease. Further such measures include the rate of change of both expiratory and inspiratory volume during a cough event. Further measures analyze segments of the cough and compare rates of change of volume at different intervals of the cough event.

In simpler cases, the amplitude of these signals (cough volume) and their slope (airflow rate) can be combined into diagnostic criteria for discriminating one type of cough from another. These parameters reflect, for example, the different depth of cough and the reflex inspiratory action at the end of the cough event. Appearance of a cough signature in the unfiltered Vt is further indicia of particular severe cough. Using these simpler severity criteria, it has been found, as illustrated by the previous example, the CF coughs may be recognized because they are likely to be of a higher severity; COPD coughs because they are likely to be of a lower severity; and PIC coughs because they are likely to be of an intermediate severity. Presence of a cough signature in the unfiltered tidal volume trace $V_t$ accompanies coughs of the highest severity.

6. EXAMPLES

This section describes speech recognition according to the methods of Section 5.5.

A. Methods

Measurement subjects included 9 men and 9 women with a mean age (±SD) of 21.3 (±1.2) years that were all physically healthy, not currently smoking cigarettes, and without history of respiratory disease. After experimental procedures were fully explained, all participants signed an approved informed consent form. Subjects then put on a RIP recording garment (1 in FIG. 1)—the LifeShirt® from VivoMetrics, Inc. (Ventura, Calif.), and the measurements were started with calibration of the respiratory sensors of the devices by breathing in and out of an 800 ml bag 7 times, filling and emptying it completely. Calibration was conducted in sitting and standing posture. Then subjects then sat quietly (quiet sitting, 4 min), talked continuously (about what their past week's experiences) (speaking, 4 min), and filled out questionnaires (writing, >4 min). They then went about their normal day and returned the next morning when the monitor was taken off.

The data stored on the memory card was downloaded to a personal analysis computer (see FIG. 1) and processed by the analysis and display software of this invention. Calibration periods were marked on the recordings and were automatically analyzed to derive K and M coefficients. Using these coefficients, Vt and Vol signals were computed from the RIP sensor signals, and a variety of breath parameters for each breath across the entire recording were computed from the Vt and Vol signals. Experimental periods (quiet sitting, speaking, writing). were marked and divided into four 1-min segments. Averages of respiratory rate, tidal volume, minute volume, inspiratory flow rate (mean), inspiratory time, expiratory time, IE-ratio, fractional inspiratory time (which is inspiratory time divided by total time), and the thoracic contribution to tidal volume were calculated and their breath-by-breath variability was indexed by coefficients of variation (CV %). The CV % was then the ratio of the standard deviations around the trend lines divided by the means after removing any linear trends. Discriminant analysis of the first three 1-min segments of the experimental periods calculated F-ratios of each parameter, % correct classification of periods, and optimal cutoff scores. Linear combinations of parameters and their classification characteristics were also determined. Discriminant functions were validated against the previously omitted, last 1-min segment data.

B. Results

Tables 1 and 2 shows respiratory parameters for minutes 1-3, rank ordered by their effect sizes for discriminating speech from two other activities. In these tables, "F" is the F-ratio with df=1, 17; "cutoff" is the optimal cutoff score for discriminating conditions; "% false" is the percent of false classifications using this cutoff.

TABLE 1 speaking vs. writing

|  | F | cutoff | % false |
| --- | --- | --- | --- |
| IE-ratio | 165.9 | 0.518 | 1.5 |
| expiratory time | 82.5 | 2.605 | 6.2 |
| fractional inspiratory time | 58.5 | 0.284 | 9.2 |
| inspiratory flow rate | 57.9 | 451.49 | 13.8 |
| CV % IE-ratio | 38.4 | 0.481 | 16.9 |
| CV % respiratory rate | 36.8 | 0.323 | 13.8 |
| inspiratory time | 30.7 | 0.893 | 44.6 |
| CV % fractional inspiratory time | 27.8 | 0.277 | 12.3 |
| tidal volume | 23.5 | 439.09 | 27.7 |
| CV % expiratory time | 14.4 | 0.319 | 16.9 |
| minute volume | 11.0 | 5.389 | 35.4 |
| respiratory rate | 10.7 | 8.743 | 43.1 |
| CV % rib contribution | 10.0 | 0.168 | 27.7 |
| CV % tidal volume | 4.0 | 0.451 | 27.7 |

TABLE 1-continued speaking vs. writing

|  | F | cutoff | % false |
| --- | --- | --- | --- |
| CV % inspiratory flow rate | 4.0 | 0.329 | 32.3 |
| CV % minute volume | 2.8 | 0.316 | 35.4 |
| CV % inspiratory time | 1.9 | 0.249 | 36.9 |
| rib contribution | 0.0 | 0.669 | 43.1 |

TABLE 2 speaking vs. quiet sitting

|  | F | cutoff | % false |
| --- | --- | --- | --- |
| CV % fractional inspiratory time | 378.1 | 0.259 | 0 |
| CV % expiratory time | 375.7 | 0.258 | 1.5 |
| CV % respiratory rate | 283.7 | 0.283 | 3 |
| CV % IE-ratio | 241.8 | 0.389 | 0 |
| IE-ratio | 236.9 | 0.523 | 1.5 |
| fractional inspiratory time | 119.1 | 0.293 | 4.5 |
| inspiratory flow rate | 88.1 | 381.69 | 7.5 |
| expiratory time | 66.6 | 2.848 | 10.4 |
| CV % inspiratory flow rate | 43.4 | 0.214 | 13.4 |
| CV % rib contribution | 42.5 | 0.081 | 11.9 |
| inspiratory time | 30.5 | 0.936 | 46.3 |
| CV % minute volume | 25.8 | 0.237 | 16.4 |
| CV % inspiratory time | 25.5 | 0.145 | 23.9 |
| minute volume | 23.8 | 7.717 | 29.9 |
| rib contribution | 23.3 | 0.598 | 37.3 |
| tidal volume | 21.8 | 647.15 | 29.9 |
| CV % tidal volume | 17.7 | 0.266 | 20.9 |
| respiratory rate | 0.1 | 8.311 | 41.8 |

Analysis revealed that the inspiratory/expiratory (IE) ratio, the fractional inspiratory time, the inspiratory flow rate, and the expiratory time (and the percentage coefficient of variation of these parameters) were all suitable for recognizing speech. A discriminant analysis for speaking vs. writing picked IE-ratio first. It distinguished speaking from writing with about 98.5% correct classification at a cutoff criterion of 0.52, and was as successful in distinguishing speaking from quiet sitting. The IE-ratio yielded the highest F-ratio for contrasting speaking from writing. These tables suggest that a composite linear function of timing, variability of timing, and volume parameters may also usefully separate speaking from the other two conditions. Some respiratory parameters, e.g., respiratory rate or rib contribution were not significantly indicative of speaking. When contrasting speaking with quiet sitting, four parameters of timing variability had the largest F-ratios, probably because quiet sitting resulted in a very regular breath-by-breath pattern of breathing. A histogram revealed that IE-ratios were approximately normally distributed within tasks and that distributions for quiet sitting and writing did nearly not overlap with those during speaking.

The invention described and claimed herein is not to be limited in scope by the preferred embodiments herein disclosed, since these embodiments are intended as illustrations of several aspects of the invention. Equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior art to the invention of the subject matter claimed herein.

What is claimed is:

1. A method for recognizing respiratory events in a monitored subject comprising:
deriving a signal (Vt) indicative of lung volume from a plurality of respiratory signals received from the monitored subject,
deriving from the Vt signal one or more temporal sequences of respiratory volume parameters, and
recognizing sigh events in dependence on at least one of the derived temporal sequences of respiratory volume parameters, wherein a breath is recognized as a sigh if that breath is not an artifact according to the true breath rule, and has volume parameters greater than a threshold sigh volume, wherein the threshold sigh volume varies in dependence on running median baseline lung volumes.

2. A method for recognizing respiratory events in a monitored subject comprising:
deriving a signal (Vt) indicative of lung volume from a plurality of respiratory signals received from the monitored subject,
deriving from the Vt signal one or more temporal sequences of respiratory parameters including peak expiratory flow (PEF) parameters, and
recognizing cough events in dependence on at least the derived temporal sequence of PEF parameters wherein a breath is recognized as a cough if that breath is not an artifact according to the true breath rule, and has a PEF greater than a threshold cough PEF, the threshold cough PEF varying in dependence on running median baseline PEF.

3. A method for recognizing respiratory events in a monitored subject comprising:
deriving a signal (Vt) indicative of lung volume from a plurality of respiratory signals received from the monitored subject,
deriving from the Vt signal one or more temporal sequences of respiratory parameters including one of more of the inspiratory/expiratory (IE) ratio, the fractional inspiratory time, the inspiratory flow rate, and the expiration time; and
recognizing speech events, wherein one or more breaths are recognized as comprising speech in dependence on the derived temporal sequences of one or more of the parameters inspiratory/expiratory (IE) ratio, the fractional inspiratory time, the inspiratory flow rate, or the expiratory time.

4. A method for recognizing respiratory events in a monitored subject comprising:
deriving a signal (Vt) indicative of lung volume from a plurality of respiratory signals received from the monitored subject,
deriving from the Vt signal one or more temporal sequences of respiratory parameters, including minute ventilation volume and peak expiratory flow (PEF) parameters; and
recognizing dyspnea events, wherein dyspnea is recognized in dependence on a ratio of these derived parameters.

5. A method for recognizing respiratory events in a monitored subject comprising:
deriving a signal (Vt) indicative of lung volume from a plurality of respiratory signals received from the monitored subject,
deriving one or more temporal sequences of respiratory parameters including the time to reach peak expiratory flow, the expiratory time, the peak expiratory flow, and the mean expiratory flow; and
recognizing changes in the ratio of forced expiratory volume in one second to vital capacity in dependence on a ratio of the derived temporal sequences of the time to reach peak expiratory flow and the expiratory time paarameters, or on a ratio of the derived temporal sequences of the peak expiratory flow and the mean expiratory flow parameters.

6. A method for recognizing respiratory events in a monitored subiect comprising:
deriving a signal (Vt) indicative of lung volume from a plurality of respiratory signals received from the monitored subject,
deriving from the Vt signal one or more temporal sequences of respiratory parameters including the peak inspiratory flow and the tidal volume, and
recognizing changes in the ratio of forced expiratory volume in one second to vital capacity in dependence on a ratio of these derived parameters.

7. A method for recognizing respiratory events in a monitored subject comprising:
deriving a signal (Vt) indicative of lung volume from a plurality of respiratory signals received from the monitored subject,
deriving from the Vt signal and a signal reflective of rib cage size one or more temporal sequences of respiratory parameters including a temporal sequence of the rib cage contribution to the tidal volume; and
recognizing changes in the ratio of forced expiratory volume in one second to vital capacity in dependence on this derived parameter.

8. A method for recognizing respiratory events in a monitored subject comprising:
deriving a signal (Vt) indicative of lung volume from a plurality of respiratory signals received from the monitored subject,
deriving one or more temporal sequences of respiratory parameters including the fraction of expiration time with thoraco-abdominal asynchrony from a signal reflective of rib cage size and a signal reflective of abdominal size, and
recognizing changes in the ratio of forced expiratory volume in one second to vital capacity in dependence this derived parameter.

9. A method for recognizing a cough in a monitored subject comprising:
recognizing a candidate sound event when an input level of a microphone signal exceeds a sound-event threshold, wherein the microphone is responsive to the subject's vocalizations,
filtering a lung volume signal (Vt) in dependence on characteristics of the candidate sound event,
recognizing a candidate respiratory event if the selected filtered tidal volume signal exhibits an expiration and a following inspiration having amplitudes greater than a amplitude threshold,
determining the occurrence of a cough if the candidate sound event coincides temporally with the candidate respiratory event.

10. The method of claim 9 wherein the sound-event threshold is a pre-determined multiple of a background noise intensity that is determined in the vicinity of the monitored subject.

11. The method of claim 10 wherein a candidate sound-event extends from the time when the input signal level exceeds the sound-event threshold to the time the time when the input level no longer exceeds the sound-event threshold.

12. The method of claim 9 wherein the amplitude threshold is individually calibrated for the monitored subject.

13. The method of claim 9 wherein the amplitude threshold is approximately 200 ml.

14. A method for recognizing a cough in a monitored subject comprising:
   recognizing a candidate sound event when an input level of a microphone signal exceeds a sound-event threshold, wherein the microphone is responsive to the subject's vocalizations,
   filtering a lung volume signal (Vt) in dependence on characteristics of the candidate sound event into a lower frequency band (LFB) if the candidate sound event has a duration longer than a duration threshold, and into a higher frequency band (HFB) if the candidate sound event has a duration shorter than the duration threshold,
   recognizing a candidate respiratory event if the selected filtered tidal volume signal exhibits an expiration and a following inspiration having amplitudes greater than a amplitude threshold, and
   determining the occurrence of a cough if the candidate sound event coincides temporally with the candidate respiratory event.

15. The method of claim 14 wherein the duration threshold is approximately 600 msec.

16. The method of claim 14 wherein the HFB excludes a range of low frequencies that are included in the LFB.

17. The method of claim 16 wherein the excluded range of frequencies is from approximately 0.4 to approximately 1.1 Hz, and wherein the frequency bands extend approximately 4.9 Hz.

18. The method of claim 9 wherein a cough is further determined only if the candidate respiratory event exhibits a sharp expiration, a minimum lung volume occurring during the central region of the associated sound event, and a sharp inspiration.

19. A method for recognizing a cough in a monitored subject comprising:
   recognizing a candidate sound event when an input level of a microphone signal exceeds a sound-event threshold, wherein the microphone is responsive to the subject's vocalizations.
   filtering a lung volume signal (Vt) in dependence on characteristics of the candidate sound event,
   recognizing a candidate respiratory event if the selected filtered tidal volume signal exhibits an expiration and a following inspiration having amplitudes greater than a amplitude threshold,
   determining the occurrence of a cough if the candidate sound event coincides temporally with the candidate respiratory event and if the candidate sound event has a pitch characteristic below a cough-pitch threshold.

20. The method of claim 19 wherein pitch characteristics are determined by short term spectral analysis of the input microphone signal.

21. The method of claim 20 wherein the short-term spectral analysis comprises determining mel-frequency cepsturm coefficients.

22. The method of claim 21 wherein the cough-pitch threshold is at met-frequency cepsturm coefficients of approximately 1.5-2.0.

23. A computer system for processing signals reflective of a monitored subject's respiration comprising: a processor, and a memory in communication with the processor, the memory comprising encoded instructions for causing the processor to perform the methods of claim 8.

24. A program product for causing a computer system to process signals reflective of a monitored subject's respiration comprising a computer readable medium with encoded instructions for causing the system to perform the method of claim 8.

* * * * *